US009319784B2

(12) United States Patent
Lu et al.

(10) Patent No.: US 9,319,784 B2
(45) Date of Patent: Apr. 19, 2016

(54) FREQUENCY-SHAPED NOISE-BASED ADAPTATION OF SECONDARY PATH ADAPTIVE RESPONSE IN NOISE-CANCELING PERSONAL AUDIO DEVICES

(71) Applicant: Cirrus Logic, Inc., Austin, TX (US)

(72) Inventors: Yang Lu, Austin, TX (US); Dayong Zhou, Austin, TX (US); Ning Li, Cedar Park, TX (US)

(73) Assignee: CIRRUS LOGIC, INC., Austin, TX (US)

( * ) Notice: Subject to any disclaimer, the term of this patent is extended or adjusted under 35 U.S.C. 154(b) by 83 days.

(21) Appl. No.: 14/252,235

(22) Filed: Apr. 14, 2014

(65) Prior Publication Data

US 2015/0296296 A1 Oct. 15, 2015

(51) Int. Cl.

| | |
|---|---|
| ***A61F 11/06*** | (2006.01) |
| ***H04R 3/00*** | (2006.01) |
| ***H04R 1/08*** | (2006.01) |

(Continued)

(52) U.S. Cl.

CPC ............ *H04R 3/002* (2013.01); *G10K 11/1784* (2013.01); *G10K 11/1788* (2013.01); *H04R 1/08* (2013.01); *H04R 1/1083* (2013.01); *H04R 3/005* (2013.01); *G10K 2210/108* (2013.01); *G10K 2210/1081* (2013.01); *G10K 2210/3028* (2013.01); *G10K 2210/3049* (2013.01); *G10K 2210/3056* (2013.01)

(58) Field of Classification Search

CPC ............ G10K 11/178; G10K 11/1784; G10K 11/1788; G10K 2210/1081

See application file for complete search history.

(56) References Cited

U.S. PATENT DOCUMENTS

| | | | |
|---|---|---|---|
| 4,020,567 | A | 5/1977 | Webster |
| 4,926,464 | A | 5/1990 | Schley-May |

(Continued)

FOREIGN PATENT DOCUMENTS

| | | | |
|---|---|---|---|
| DE | 102011013343 | A1 | 9/2012 |
| EP | 0412902 | | 2/1991 |

(Continued)

OTHER PUBLICATIONS

U.S. Appl. No. 13/686,353, filed Nov. 27, 2012, Hendrix, et al.

(Continued)

*Primary Examiner* — Simon Sing

(74) *Attorney, Agent, or Firm* — Mitch Harris, Atty at Law, LLC; Andrew M. Harris

(57) ABSTRACT

A personal audio device includes an adaptive noise canceling (ANC) circuit that adaptively generates an anti-noise signal from a reference microphone signal and injects the anti-noise signal into the speaker or other transducer output to cause cancellation of ambient audio sounds. An error microphone is also provided proximate the speaker to provide an error signal indicative of the effectiveness of the noise cancellation. A secondary path estimating adaptive filter is used to estimate the electro-acoustical path from the noise canceling circuit through the transducer so that source audio can be removed from the error signal. Noise is injected so that the adaptation of the secondary path estimating adaptive filter can be maintained, irrespective of the presence and amplitude of the source audio. The noise is shaped by a noise shaping filter that has a response controlled in conformity with at least one parameter of the secondary path response.

24 Claims, 11 Drawing Sheets

(51) Int. Cl.
*G10K 11/178* (2006.01)
*H04R 1/10* (2006.01)

(56) References Cited

U.S. PATENT DOCUMENTS 4,998,241 A 3/1991 Brox et al.
5,018,202 A 5/1991 Takahashi
5,021,753 A 6/1991 Chapman
5,044,373 A 9/1991 Northeved et al.
5,251,263 A 10/1993 Andrea et al.
5,278,913 A 1/1994 Delfosse et al.
5,321,759 A 6/1994 Yuan
5,337,365 A 8/1994 Hamabe et al.
5,359,662 A 10/1994 Yuan et al.
5,386,477 A 1/1995 Popovich et al.
5,410,605 A 4/1995 Sawada et al.
5,425,105 A 6/1995 Lo et al.
5,445,517 A 8/1995 Kondou et al.
5,465,413 A 11/1995 Enge et al.
5,481,615 A 1/1996 Eatwell et al.
5,548,681 A 8/1996 Gleaves et al.
5,550,925 A 8/1996 Hori et al.
5,559,893 A 9/1996 Krokstad et al.
5,586,190 A 12/1996 Trantow et al.
5,640,450 A 6/1997 Watanabe
5,668,747 A 9/1997 Ohashi
5,687,075 A 11/1997 Stothers
5,696,831 A 12/1997 Inanaga et al.
5,699,437 A 12/1997 Finn
5,706,344 A 1/1998 Finn
5,740,256 A 4/1998 Castello Da Costa et al.
5,768,124 A 6/1998 Stothers et al.
5,815,582 A 9/1998 Claybaugh et al.
5,832,095 A 11/1998 Daniels
5,852,667 A 12/1998 Pan et al.
5,909,498 A 6/1999 Smith
5,940,519 A 8/1999 Kuo
5,946,391 A 8/1999 Dragwidge et al.
5,991,418 A 11/1999 Kuo
6,041,126 A 3/2000 Terai et al.
6,118,878 A 9/2000 Jones
6,181,801 B1 1/2001 Puthuff et al.
6,219,427 B1 4/2001 Kates et al.
6,278,786 B1 8/2001 McIntosh
6,282,176 B1 8/2001 Hemkumar
6,304,179 B1 10/2001 Lotito et al.
6,418,228 B1 7/2002 Terai et al.
6,434,246 B1 8/2002 Kates et al.
6,434,247 B1 8/2002 Kates et al.
6,445,799 B1 9/2002 Taenzer et al.
6,522,746 B1 2/2003 Marchok et al.
6,542,436 B1 4/2003 Myllyla
6,650,701 B1 11/2003 Hsiang et al.
6,683,960 B1 1/2004 Fujii et al.
6,738,482 B1 5/2004 Jaber
6,766,292 B1 7/2004 Chandran
6,768,795 B2 7/2004 Feltstrom et al.
6,792,107 B2 9/2004 Tucker et al.
6,850,617 B1 2/2005 Weigand
6,940,982 B1 9/2005 Watkins
7,016,504 B1 3/2006 Shennib
7,058,463 B1 6/2006 Ruha et al.
7,103,188 B1 9/2006 Jones
7,181,030 B2 2/2007 Rasmussen et al.
7,330,739 B2 2/2008 Somayajula
7,365,669 B1 4/2008 Melanson
7,466,838 B1 12/2008 Mosely
7,680,456 B2 3/2010 Muhammad et al.
7,742,746 B2 6/2010 Xiang et al.
7,742,790 B2 6/2010 Konchitsky et al.
7,817,808 B2 10/2010 Konchitsky et al.
7,953,231 B2 5/2011 Ishida
8,019,050 B2 9/2011 Mactavish et al.
D666,169 S 8/2012 Tucker et al.
8,249,262 B2 8/2012 Chua et al.
8,251,903 B2 8/2012 LeBoeuf et al.
8,290,537 B2 10/2012 Lee et al.
8,325,934 B2 12/2012 Kuo
8,331,604 B2 12/2012 Saito et al.
8,379,884 B2 2/2013 Horibe et al.
8,401,200 B2 3/2013 Tiscareno et al.
8,442,251 B2 5/2013 Jensen et al.
8,559,661 B2 10/2013 Tanghe
8,600,085 B2 12/2013 Chen et al.
8,775,172 B2 7/2014 Konchitsky et al.
8,804,974 B1 8/2014 Melanson
8,831,239 B2 9/2014 Bakalos
8,842,848 B2 9/2014 Donaldson et al.
8,855,330 B2 10/2014 Taenzer
8,908,877 B2 12/2014 Abdollahzadeh Milani et al.
9,066,176 B2 6/2015 Hendrix et al.
9,071,724 B2 6/2015 Do et al.
9,129,586 B2 9/2015 Bajic et al.
2001/0053228 A1 12/2001 Jones
2002/0003887 A1 1/2002 Zhang et al.
2003/0063759 A1 4/2003 Brennan et al.
2003/0072439 A1 4/2003 Gupta
2003/0185403 A1 10/2003 Sibbald
2004/0047464 A1 3/2004 Yu et al.
2004/0120535 A1 6/2004 Woods
2004/0165736 A1 8/2004 Hetherington et al.
2004/0167777 A1 8/2004 Hetherington et al.
2004/0202333 A1 10/2004 Csermak et al.
2004/0240677 A1 12/2004 Onishi et al.
2004/0242160 A1 12/2004 Ichikawa et al.
2004/0264706 A1 12/2004 Ray et al.
2005/0004796 A1 1/2005 Trump et al.
2005/0018862 A1 1/2005 Fisher
2005/0117754 A1 6/2005 Sakawaki
2005/0207585 A1 9/2005 Christoph
2005/0240401 A1 10/2005 Ebenezer
2006/0035593 A1 2/2006 Leeds
2006/0055910 A1 3/2006 Lee
2006/0069556 A1 3/2006 Nadjar et al.
2006/0153400 A1 7/2006 Fujita et al.
2006/0159282 A1 7/2006 Borsch
2006/0161428 A1 7/2006 Fouret
2006/0251266 A1 11/2006 Saunders et al.
2007/0030989 A1 2/2007 Kates
2007/0033029 A1 2/2007 Sakawaki
2007/0038441 A1 2/2007 Inoue et al.
2007/0047742 A1 3/2007 Taenzer et al.
2007/0053524 A1 3/2007 Haulick et al.
2007/0076896 A1 4/2007 Hosaka et al.
2007/0154031 A1 7/2007 Avendano et al.
2007/0258597 A1 11/2007 Rasmussen et al.
2007/0297620 A1 12/2007 Choy
2008/0019548 A1 1/2008 Avendano
2008/0101589 A1 5/2008 Horowitz et al.
2008/0107281 A1 5/2008 Togami et al.
2008/0144853 A1 6/2008 Sommerfeldt et al.
2008/0177532 A1 7/2008 Greiss et al.
2008/0181422 A1 7/2008 Christoph
2008/0226098 A1 9/2008 Haulick et al.
2008/0240413 A1 10/2008 Mohammad et al.
2008/0240455 A1 10/2008 Inoue et al.
2008/0240457 A1 10/2008 Inoue et al.
2008/0269926 A1 10/2008 Xiang et al.
2009/0012783 A1 1/2009 Klein
2009/0034748 A1 2/2009 Sibbald
2009/0041260 A1 2/2009 Jorgensen et al.
2009/0046867 A1 2/2009 Clemow
2009/0060222 A1 3/2009 Jeong et al.
2009/0080670 A1 3/2009 Solbeck et al.
2009/0086990 A1 4/2009 Christoph
2009/0175466 A1 7/2009 Elko et al.
2009/0196429 A1 8/2009 Ramakrishnan et al.
2009/0220107 A1 9/2009 Every et al.
2009/0238369 A1 9/2009 Ramakrishnan et al.
2009/0245529 A1 10/2009 Asada et al.
2009/0254340 A1 10/2009 Sun et al.
2009/0290718 A1 11/2009 Kahn et al.
2009/0296965 A1 12/2009 Kojima
2009/0304200 A1 12/2009 Kim et al.

(56) References Cited

U.S. PATENT DOCUMENTS

| | | | |
|---|---|---|---|
| 2009/0311979 A1 | 12/2009 | Husted et al. | |
| 2010/0002891 A1 | 1/2010 | Shiraishi et al. | |
| 2010/0014683 A1 | 1/2010 | Maeda et al. | |
| 2010/0014685 A1 | 1/2010 | Wurm | |
| 2010/0061564 A1 | 3/2010 | Clemow et al. | |
| 2010/0069114 A1 | 3/2010 | Lee et al. | |
| 2010/0082339 A1 | 4/2010 | Konchitsky et al. | |
| 2010/0098263 A1 | 4/2010 | Pan et al. | |
| 2010/0098265 A1 | 4/2010 | Pan et al. | |
| 2010/0124336 A1 | 5/2010 | Shridhar et al. | |
| 2010/0124337 A1 | 5/2010 | Wertz et al. | |
| 2010/0131269 A1 | 5/2010 | Park et al. | |
| 2010/0142715 A1 | 6/2010 | Goldstein et al. | |
| 2010/0150367 A1 | 6/2010 | Mizuno | |
| 2010/0158330 A1 | 6/2010 | Guissin et al. | |
| 2010/0166203 A1 | 7/2010 | Peissig et al. | |
| 2010/0195838 A1 | 8/2010 | Bright | |
| 2010/0195844 A1 | 8/2010 | Christoph et al. | |
| 2010/0207317 A1 | 8/2010 | Iwami et al. | |
| 2010/0239126 A1 | 9/2010 | Grafenberg et al. | |
| 2010/0246855 A1 | 9/2010 | Chen | |
| 2010/0260345 A1 | 10/2010 | Shridhar et al. | |
| 2010/0266137 A1 | 10/2010 | Sibbald et al. | |
| 2010/0272276 A1 | 10/2010 | Carreras et al. | |
| 2010/0272283 A1 | 10/2010 | Carreras et al. | |
| 2010/0274564 A1 | 10/2010 | Bakalos et al. | |
| 2010/0284546 A1 | 11/2010 | DeBrunner et al. | |
| 2010/0291891 A1 | 11/2010 | Ridgers et al. | |
| 2010/0296666 A1 | 11/2010 | Lin | |
| 2010/0296668 A1 | 11/2010 | Lee et al. | |
| 2010/0310086 A1 | 12/2010 | Magrath et al. | |
| 2010/0316225 A1 | 12/2010 | Saito et al. | |
| 2010/0322430 A1 | 12/2010 | Isberg | |
| 2011/0007907 A1 | 1/2011 | Park et al. | |
| 2011/0026724 A1 | 2/2011 | Doclo | |
| 2011/0106533 A1 | 5/2011 | Yu | |
| 2011/0116654 A1 | 5/2011 | Chan et al. | |
| 2011/0129098 A1 | 6/2011 | Delano et al. | |
| 2011/0130176 A1 | 6/2011 | Magrath et al. | |
| 2011/0142247 A1 | 6/2011 | Fellers et al. | |
| 2011/0144984 A1 | 6/2011 | Konchitsky | |
| 2011/0158419 A1 | 6/2011 | Theverapperuma et al. | |
| 2011/0206214 A1 | 8/2011 | Christoph et al. | |
| 2011/0222698 A1 | 9/2011 | Asao et al. | |
| 2011/0249826 A1 | 10/2011 | Van Leest | |
| 2011/0288860 A1 | 11/2011 | Schevciw et al. | |
| 2011/0293103 A1 | 12/2011 | Park et al. | |
| 2011/0299695 A1 | 12/2011 | Nicholson | |
| 2011/0305347 A1 | 12/2011 | Wurm | |
| 2011/0317848 A1 | 12/2011 | Ivanov et al. | |
| 2012/0135787 A1 | 5/2012 | Kusunoki et al. | |
| 2012/0140917 A1 | 6/2012 | Nicholson et al. | |
| 2012/0140942 A1 | 6/2012 | Loeda | |
| 2012/0140943 A1 | 6/2012 | Hendrix et al. | |
| 2012/0148062 A1 | 6/2012 | Scarlett et al. | |
| 2012/0155666 A1 | 6/2012 | Nair | |
| 2012/0170766 A1 | 7/2012 | Alves et al. | |
| 2012/0207317 A1 | 8/2012 | Milani et al. | |
| 2012/0215519 A1 | 8/2012 | Park et al. | |
| 2012/0250873 A1 | 10/2012 | Bakalos et al. | |
| 2012/0259626 A1 | 10/2012 | Li et al. | |
| 2012/0263317 A1 | 10/2012 | Shin et al. | |
| 2012/0281850 A1 | 11/2012 | Hyatt | |
| 2012/0300955 A1* | 11/2012 | Iseki .................. | G10K 11/1786 381/71.4 |
| 2012/0300958 A1 | 11/2012 | Klemmensen | |
| 2012/0300960 A1 | 11/2012 | Mackay et al. | |
| 2012/0308021 A1 | 12/2012 | Kwatra et al. | |
| 2012/0308024 A1 | 12/2012 | Alderson et al. | |
| 2012/0308025 A1 | 12/2012 | Hendrix et al. | |
| 2012/0308026 A1 | 12/2012 | Kamath et al. | |
| 2012/0308027 A1 | 12/2012 | Kwatra | |
| 2012/0308028 A1 | 12/2012 | Kwatra et al. | |
| 2012/0310640 A1 | 12/2012 | Kwatra et al. | |
| 2013/0010982 A1 | 1/2013 | Elko et al. | |
| 2013/0083939 A1 | 4/2013 | Fellers et al. | |
| 2013/0195282 A1* | 8/2013 | Ohita ................. | G10K 11/1782 381/71.2 |
| 2013/0243198 A1 | 9/2013 | Van Rumpt | |
| 2013/0243225 A1 | 9/2013 | Yokota | |
| 2013/0272539 A1 | 10/2013 | Kim et al. | |
| 2013/0287218 A1 | 10/2013 | Alderson et al. | |
| 2013/0287219 A1 | 10/2013 | Hendrix et al. | |
| 2013/0301842 A1 | 11/2013 | Hendrix et al. | |
| 2013/0301846 A1 | 11/2013 | Alderson et al. | |
| 2013/0301847 A1 | 11/2013 | Alderson et al. | |
| 2013/0301848 A1 | 11/2013 | Zhou et al. | |
| 2013/0301849 A1 | 11/2013 | Alderson et al. | |
| 2013/0315403 A1 | 11/2013 | Samuelsson | |
| 2013/0343556 A1 | 12/2013 | Bright | |
| 2013/0343571 A1 | 12/2013 | Rayala et al. | |
| 2014/0016803 A1 | 1/2014 | Puskarich | |
| 2014/0036127 A1 | 2/2014 | Pong et al. | |
| 2014/0044275 A1 | 2/2014 | Goldstein et al. | |
| 2014/0050332 A1 | 2/2014 | Nielsen et al. | |
| 2014/0072134 A1 | 3/2014 | Po et al. | |
| 2014/0072135 A1 | 3/2014 | Bajic et al. | |
| 2014/0086425 A1 | 3/2014 | Jensen et al. | |
| 2014/0146976 A1 | 5/2014 | Rundle | |
| 2014/0169579 A1 | 6/2014 | Azmi | |
| 2014/0177851 A1 | 6/2014 | Kitazawa et al. | |
| 2014/0211953 A1 | 7/2014 | Alderson et al. | |
| 2014/0270222 A1 | 9/2014 | Hendrix et al. | |
| 2014/0270223 A1 | 9/2014 | Li et al. | |
| 2014/0270224 A1 | 9/2014 | Zhou et al. | |
| 2014/0294182 A1 | 10/2014 | Axelsson | |
| 2014/0307887 A1 | 10/2014 | Alderson | |
| 2014/0307888 A1 | 10/2014 | Alderson et al. | |
| 2014/0307890 A1 | 10/2014 | Zhou et al. | |
| 2014/0314244 A1 | 10/2014 | Yong et al. | |
| 2014/0314246 A1 | 10/2014 | Hellman | |
| 2014/0314247 A1 | 10/2014 | Zhang | |
| 2014/0369517 A1 | 12/2014 | Zhou et al. | |
| 2015/0078572 A1 | 3/2015 | Milani et al. | |
| 2015/0092953 A1 | 4/2015 | Abdollahzadeh Milani et al. | |
| 2015/0161981 A1 | 6/2015 | Kwatra | |

FOREIGN PATENT DOCUMENTS

| | | | |
|---|---|---|---|
| EP | 1691577 | A2 | 8/2006 |
| EP | 1880699 | A2 | 1/2008 |
| EP | 1947642 | A1 | 7/2008 |
| EP | 2133866 | A1 | 12/2009 |
| EP | 2216774 | A1 | 8/2010 |
| EP | 2237573 | A1 | 10/2010 |
| EP | 2395500 | A1 | 12/2011 |
| EP | 2395501 | A1 | 12/2011 |
| EP | 2551845 | | 1/2013 |
| EP | 2583074 | | 4/2013 |
| GB | 2401744 | A | 11/2004 |
| GB | 2436657 | | 10/2007 |
| GB | 2455821 | A | 6/2009 |
| GB | 2455824 | A | 6/2009 |
| GB | 2455828 | A | 6/2009 |
| GB | 2484722 | A | 4/2012 |
| JP | H06-186985 | A | 7/1994 |
| JP | 07104769 | | 4/1995 |
| JP | 07240989 | | 9/1995 |
| JP | 07325588 | | 12/1995 |
| WO | WO 9113429 | | 9/1991 |
| WO | WO 9911045 | | 3/1999 |
| WO | WO 03/015074 | A1 | 2/2003 |
| WO | WO 03015275 | A1 | 2/2003 |
| WO | WO 2004009007 | A1 | 1/2004 |
| WO | WO 2004017303 | A1 | 2/2004 |
| WO | WO 2006128768 | | 12/2006 |
| WO | WO 2007007916 | A1 | 1/2007 |
| WO | WO 2007011337 | | 1/2007 |
| WO | WO 2007110807 | A2 | 10/2007 |
| WO | WO 2007113487 | A1 | 11/2007 |
| WO | WO 2010117714 | A1 | 10/2010 |
| WO | WO 2010131154 | A1 | 11/2010 |
| WO | WO 2012134874 | A1 | 10/2012 |
| WO | WO 2014158475 | | 10/2014 |

(56) References Cited

FOREIGN PATENT DOCUMENTS

| | | |
|---|---|---|
| WO | WO 2014168685 | 10/2014 |
| WO | WO 2014172005 | 10/2014 |
| WO | WO 2014172006 | 10/2014 |
| WO | WO 2014172010 | 10/2014 |
| WO | WO 2014172019 | 10/2014 |
| WO | WO 2014172021 | 10/2014 |
| WO | WO 2014200787 | 12/2014 |
| WO | WO 2015038255 A1 | 3/2015 |
| WO | WO 2015088639 | 6/2015 |
| WO | WO 2015088651 | 6/2015 |
| WO | WO 2015088653 | 6/2015 |

OTHER PUBLICATIONS

U.S. Appl. No. 13/794,931, filed Mar. 12, 2013, Lu, et al.
U.S. Appl. No. 13/794,979, filed Mar. 12, 2013, Alderson, et al.
U.S. Appl. No. 13/968,007, filed Aug. 15, 2013, Hendrix, et al.
U.S. Appl. No. 14/029,159, filed Sep. 17, 2013, Li, et al.
U.S. Appl. No. 14/062,951, filed Oct. 25, 2013, Zhou, et al.
U.S. Appl. No. 14/197,814, filed Mar. 5, 2014, Kaller, et al.
U.S. Appl. No. 14/210,537, filed Mar. 14, 2014, Abdollahzadeh Milani, et.
U.S. Appl. No. 14/210,589, filed Mar. 14, 2014, Abdollahzadeh Milani, et.
Black, John W., "An Application of Side-Tone in Subjective Tests of Microphones and Headsets", Project Report No. NM 001 064.01.20, Research Report of the U.S. Naval School of Aviation Medicine, Feb. 1, 1954, 12 pages (pp. 1-12 in pdf), Pensacola, FL, US.
Peters, Robert W., "The Effect of High-Pass and Low-Pass Filtering of Side-Tone Upon Speaker Intelligibility", Project Report No. NM 001 064.01.25, Research Report of the U.S. Naval School of Aviation Medicine, Aug. 16, 1954, 13 pages (pp. 1-13 in pdf), Pensacola, FL, US.
Lane, et al., "Voice Level: Autophonic Scale, Perceived Loudness, and the Effects of Sidetone", The Journal of the Acoustical Society of America, Feb. 1961, pp. 160-167, vol. 33, No. 2., Cambridge, MA, US.
Liu, et al., "Compensatory Responses to Loudness-shifted Voice Feedback During Production of Mandarin Speech", Journal of the Acoustical Society of America, Oct. 2007, pp. 2405-2412, vol. 122, No. 4.
Paepcke, et al., "Yelling in the Hall: Using Sidetone to Address a Problem with Mobile Remote Presence Systems", Symposium on User Interface Software and Technology, Oct. 16-19, 2011, 10 pages (pp. 1-10 in pdf), Santa Barbara, CA, US.
Therrien, et al., "Sensory Attenuation of Self-Produced Feedback: The Lombard Effect Revisited", PLOS One, Nov. 2012, pp. 1-7, vol. 7, Issue 11, e49370, Ontario, Canada.
Pfann, et al., "LMS Adaptive Filtering with Delta-Sigma Modulated Input Signals," IEEE Signal Processing Letters, Apr. 1998, pp. 95-97, vol. 5, No. 4, IEEE Press, Piscataway, NJ.
Toochinda, et al. "A Single-Input Two-Output Feedback Formulation for ANC Problems," Proceedings of the 2001 American Control Conference, Jun. 2001, pp. 923-928, vol. 2, Arlington, VA.
Kuo, et al., "Active Noise Control: A Tutorial Review," Proceedings of the IEEE, Jun. 1999, pp. 943-973, vol. 87, No. 6, IEEE Press, Piscataway, NJ.
Johns, et al., "Continuous-Time LMS Adaptive Recursive Filters," IEEE Transactions on Circuits and Systems, Jul. 1991, pp. 769-778, vol. 38, No. 7, IEEE Press, Piscataway, NJ.
Shoval, et al., "Comparison of DC Offset Effects in Four LMS Adaptive Algorithms," IEEE Transactions on Circuits and Systems II: Analog and Digital Processing, Mar. 1995, pp. 176-185, vol. 42, Issue 3, IEEE Press, Piscataway, NJ.
Mali, Dilip, "Comparison of DC Offset Effects on LMS Algorithm and its Derivatives," International Journal of Recent Trends in Engineering, May 2009, pp. 323-328, vol. 1, No. 1, Academy Publisher.
Kates, James M., "Principles of Digital Dynamic Range Compression," Trends in Amplification, Spring 2005, pp. 45-76, vol. 9, No. 2, Sage Publications.
Gao, et al., "Adaptive Linearization of a Loudspeaker," IEEE International Conference on Acoustics, Speech, and Signal Processing, Apr. 14-17, 1991, pp. 3589-3592, Toronto, Ontario, CA.
Silva, et al., "Convex Combination of Adaptive Filters With Different Tracking Capabilities," IEEE International Conference on Acoustics, Speech, and Signal Processing, Apr. 15-20, 2007, pp. III 925-928, vol. 3, Honolulu, HI, USA.
Akhtar, et al., "A Method for Online Secondary Path Modeling in Active Noise Control Systems," IEEE International Symposium on Circuits and Systems, May 23-26, 2005, pp. 264-267, vol. 1, Kobe, Japan.
Davari, et al., "A New Online Secondary Path Modeling Method for Feedforward Active Noise Control Systems," IEEE International Conference on Industrial Technology, Apr. 21-24, 2008, pp. 1-6, Chengdu, China.
Lan, et al., "An Active Noise Control System Using Online Secondary Path Modeling With Reduced Auxiliary Noise," IEEE Signal Processing Letters, Jan. 2002, pp. 16-18, vol. 9, Issue 1, IEEE Press, Piscataway, NJ.
Liu, et al., "Analysis of Online Secondary Path Modeling With Auxiliary Noise Scaled by Residual Noise Signal," IEEE Transactions on Audio, Speech and Language Processing, Nov. 2010, pp. 1978-1993, vol. 18, Issue 8, IEEE Press, Piscataway, NJ.
U.S. Appl. No. 14/228,322, filed Mar. 28, 2014, Alderson, et al.
U.S. Appl. No. 13/762,504, filed Feb. 8, 2013, Abdollahzadeh Milani, et al.
U.S. Appl. No. 13/721,832, filed Dec. 20, 2012, Lu, et al.
U.S. Appl. No. 13/724,656, filed Dec. 21, 2012, Lu, et al.
U.S. Appl. No. 13/968,013, filed Aug. 15, 2013, Abdollahzadeh Milani, et al.
U.S. Appl. No. 13/924,935, filed Jun. 24, 2013, Hellman.
U.S. Appl. No. 13/896,526, filed May 17, 2013, Naderi.
U.S. Appl. No. 14/101,955, filed Dec. 10, 2013, Alderson.
U.S. Appl. No. 14/101,777, filed Dec. 10, 2013, Alderson et al.
Abdollahzadeh Milani, et al., "On Maximum Achievable Noise Reduction in ANC Systems",2010 IEEE International Conference on Acoustics Speech and Signal Processing, Mar. 14-19, 2010, pp. 349-352, Dallas, TX, US.
Cohen, Israel, "Noise Spectrum Estimation in Adverse Environments: Improved Minima Controlled Recursive Averaging", IEEE Transactions on Speech and Audio Processing, Sep. 2003, pp. 1-11, vol. 11, Issue 5, Piscataway, NJ, US.
Ryan, et al., "Optimum Near-Field Performance of Microphone Arrays Subject to a Far-Field Beampattern Constraint", J. Acoust. Soc. Am., Nov. 2000, pp. 2248-2255, 108 (5), Pt. 1, Ottawa, Ontario, Canada.
Cohen, et al., "Noise Estimation by Minima Controlled Recursive Averaging for Robust Speech Enhancement", IEEE Signal Processing Letters, Jan. 2002, pp. 12-15, vol. 9, No. 1, Piscataway, NJ, US.
Martin, Rainer, "Noise Power Spectral Density Estimation Based on Optimal Smoothing and Minimum Statistics", IEEE Transactions on Speech and Audio Processing, Jul. 2001, pp. 504-512, vol. 9, No. 5, Piscataway, NJ, US.
Martin, Rainer, "Spectral Subtraction Based on Minimum Statistics", Signal Processing VII Theories and Applications, Proceedings of EUSIPCO-94, 7th European Signal Processing Conference, Sep. 13-16, 1994, pp. 1182-1185, vol. III, Edinburgh, Scotland, U.K.
Booij, et al., "Virtual sensors for local, three dimensional, broadband multiple-channel active noise control and the effects on the quiet zones", Proceedings of the International Conference on Noise and Vibration Engineering, ISMA 2010, Sep. 20-22, 2010, pp. 151-166, Leuven.
Kuo, et al., "Residual noise shaping technique for active noise control systems", J. Acoust. Soc. Am. 95 (3), Mar. 1994, pp. 1665-1668.
Lopez-Caudana, Edgar Omar, "Active Noise Cancellation: The Unwanted Signal and The Hybrid Solution", Adaptive Filtering Applications, Dr. Lino Garcia (Ed.), Jul. 2011, pp. 49-84, ISBN: 978-953-307-306-4, InTech.
Senderowicz, et al., "Low-Voltage Double-Sampled Delta-Sigma Converters", IEEE Journal on Solid-State Circuits, Dec. 1997, pp. 1907-1919, vol. 32, No. 12, Piscataway, NJ.

(56) References Cited

OTHER PUBLICATIONS

Hurst, et al., “An improved double sampling scheme for switched-capacitor delta-sigma modulators”, 1992 IEEE Int. Symp. on Circuits and Systems, May 10-13, 1992, vol. 3, pp. 1179-1182, San Diego, CA.
U.S. Appl. No. 14/578,567, filed Dec. 22, 2014, Kwatra, et al.
Widrow, B., et al., Adaptive Noise Cancelling; Principles and Applications, Proceedings of the IEEE, Dec. 1975, pp. 1692-1716, vol. 63, No. 13, IEEE, New York, NY, US.
Morgan, et al., A Delayless Subband Adaptive Filter Architecture, IEEE Transactions on Signal Processing, IEEE Service Center, Aug. 1995, pp. 1819-1829, vol. 43, No. 8, New York, NY, US.
U.S. Appl. No. 14/656,124, filed Mar. 12, 2015, Hendrix, et al.
International Search Report and Written Opinion in PCT/US2015/022113, mailed on Jul. 23, 2015, 13 pages (pp. 1-13 in pdf).
U.S. Appl. No. 14/734,321, filed Jun. 9, 2015, Alderson, et al.
Campbell, Mikey, “Apple looking into self-adjusting earbud headphones with noise cancellation tech”, Apple Insider, Jul. 4, 2013, pp. 1-10 (10 pages in pdf), downloaded on May 14, 2014 from http://appleinsider.com/articles/13/07/04/apple-looking-into-self-adjusting-earbud-headphones-with-noise-cancellation-tech.
Jin, et al. “A simultaneous equation method-based online secondary path modeling algorithm for active noise control”, Journal of Sound and Vibration, Apr. 25, 2007, pp. 455-474, vol. 303, No. 3-5, London, GB.
Erkelens, et al., “Tracking of Nonstationary Noise Based on Data-Driven Recursive Noise Power Estimation”, IEEE Transactions on Audio Speech and Language Processing, Aug. 2008, pp. 1112-1123, vol. 16, No. 6, Piscataway, NJ, US.
Rao, et al., “A Novel Two State Single Channel Speech Enhancement Technique”, India Conference (INDICON) 2011 Annual IEEE, IEEE, Dec. 2011, 6 pages (pp. 1-6 in pdf), Piscataway, NJ, US.
Rangachari, et al., “A noise-estimation algorithm for highly non-stationary environments”, Speech Communication, Feb. 2006, pp. 220-231, vol. 48, No. 2. Elsevier Science Publishers.
Parkins, et al., “Narrowband and broadband active control in an enclosure using the acoustic energy density”, J. Acoust. Soc. Am. Jul. 2000, pp. 192-203, vol. 108, issue 1, US.
Feng, et al.., “A broadband self-tuning active noise equaliser”, Signal Processing, Oct. 1, 1997, pp. 251-256, vol. 62, No. 2, Elsevier Science Publishers B.V. Amsterdam, NL.
Zhang, et al., “A Robust Online Secondary Path Modeling Method with Auxiliary Noise Power Scheduling Strategy and Norm Constraint Manipulation”, IEEE Transactions on Speech and Audio Processing, IEEE Service Center, Jan. 1, 2003, pp. 45-53, vol. 11, No. 1, NY.
Lopez-Gaudana, et al., “A hybrid active noise cancelling with secondary path modeling”, 51st Midwest Symposium on Circuits and Systems, MWSCAS 2008, Aug. 10-13, 2008, pp. 277-280, IEEE, Knoxville, TN.
U.S. Appl. No. 14/840,831, Aug. 31, 2015, Hendrix, et al.
Office Action in U.S. Appl. No. 14/026,021 mailed on Sep. 1, 2015, 9 pages (pp. 1-9 in pdf).
Amendment to Office Action in U.S. Appl. No. 14/026,021, 14 pages (pp. 1-14 in pdf).
International Patent Application No. PCT/US2014/049600, International Search Report and Written Opinion, Jan. 14, 2015, 12 pages.
International Patent Application No. PCT/US2014/061753, International Search Report and Written Opinion, Feb. 9, 2015, 8 pages.
International Patent Application No. PCT/US2014/061548, International Search Report and Written Opinion, Feb. 12, 2015, 13 pages.
International Patent Application No. PCT/US2014/060277, International Search Report and Written Opinion, Mar. 9, 2015, 11 pages.
International Patent Application No. PCT/US2014/017112, International Search Report and Written Opinion, May 8, 2015, 22 pages.
International Patent Application No. PCT/US2014/017096, International Search Report and Written Opinion, May 27, 2015, 11 pages.
International Patent Application No. PCT/US2014/017343, International Search Report and Written Opinion, Aug. 8, 2014, 22 pages.
International Patent Application No. PCT/US2014/018027, International Search Report and Written Opinion, Sep. 4, 2014, 14 pages.
International Patent Application No. PCT/US2014/017374, International Search Report and Written Opinion, Sep. 8, 2014, 13 pages.
International Patent Application No. PCT/US2014/019395, International Search Report and Written Opinion, Sep. 9, 2014, 14 pages.
International Patent Application No. PCT/US2014/019469, International Search Report and Written Opinion, Sep. 12, 2014, 13 pages.
International Patent Application No. PCT/US2014/040999, International Search Report and Written Opinion, Oct. 18, 2014, 12 pages.
International Patent Application No. PCT/US2013/049407, International Search Report and Written Opinion, Jun. 18, 2014, 13 pages.
Rafaely, Boaz, “Active Noise Reducing Headset—an Overview”, The 2001 International Congress and Exhibition on Noise Control Engineering, Aug. 27-30, 2001, 10 pages (pp. 1-10 in pdf), The Netherlands.
Ray, et al., “Hybrid Feedforward-Feedback Active Noise Reduction for Hearing Protection and Communication”, The Journal of the Acoustical Society of America, American Institute of Physics for the Acoustical Society of America, Jan. 2006, pp. 2026-2036, vol. 120, No. 4, New York, NY, US.

* cited by examiner

FREQUENCY-SHAPED NOISE-BASED ADAPTATION OF SECONDARY PATH ADAPTIVE RESPONSE IN NOISE-CANCELING PERSONAL AUDIO DEVICES

BACKGROUND OF THE INVENTION

1. Field of the Invention

The present invention relates generally to personal audio devices such as wireless telephones that include adaptive noise cancellation (ANC), and more specifically, to control of ANC in a personal audio device that uses injected noise having a frequency-shaped noise-based adaptation of a secondary path estimate.

2. Background of the Invention

Wireless telephones, such as mobile/cellular telephones, headphones, and other consumer audio devices are in widespread use. Performance of such devices with respect to intelligibility can be improved by providing noise canceling using a microphone to measure ambient acoustic events and then using signal processing to insert an anti-noise signal into the output of the device to cancel the ambient acoustic events.

Noise canceling operation can be improved by measuring the transducer output of a device at the transducer to determine the effectiveness of the noise canceling using an error microphone. The measured output of the transducer is ideally the source audio, e.g., the audio provided to a headset for reproduction, or downlink audio in a telephone and/or playback audio in either a dedicated audio player or a telephone, since the noise canceling signal(s) are ideally canceled by the ambient noise at the location of the transducer. To remove the source audio from the error microphone signal, the secondary path from the transducer through the error microphone can be estimated and used to filter the source audio to the correct phase and amplitude for subtraction from the error microphone signal. However, when source audio is absent or low in amplitude, the secondary path estimate cannot typically be updated.

Therefore, it would be desirable to provide a personal audio device, including wireless telephones, that provides noise cancellation using a secondary path estimate to measure the output of the transducer and that can continuously adapt the secondary path estimate independent of whether source audio of sufficient amplitude is present.

SUMMARY OF THE INVENTION

The above-stated objective of providing a personal audio device providing noise cancelling including a secondary path estimate that can be adapted continuously whether or not source audio of sufficient amplitude is present, is accomplished in a noise-canceling personal audio device, including noise-canceling headphones, a method of operation, and an integrated circuit.

The personal audio device includes a housing, with a transducer mounted on the housing for reproducing an audio signal that includes both source audio for providing to a listener and an anti-noise signal for countering the effects of ambient audio sounds in an acoustic output of the transducer. A reference microphone is mounted on the housing to provide a reference microphone signal indicative of the ambient audio sounds. The personal audio device further includes an adaptive noise-canceling (ANC) processing circuit within the housing for adaptively generating an anti-noise signal from the reference microphone signal such that the anti-noise signal causes substantial cancellation of the ambient audio sounds. An error microphone is included for controlling the adaptation of the anti-noise signal to cancel the ambient audio sounds and for correcting for the electro-acoustical path from the output of the processing circuit through the transducer. The ANC processing circuit injects noise when the source audio, e.g., downlink audio in telephones and/or playback audio in media players or telephones, is at such a low level that the secondary path estimating adaptive filter cannot properly continue adaptation. A controllable filter frequency-shapes the noise in conformity with at least one parameter of the secondary path response, so that audibility of the noise output by the transducer is reduced, while providing noise of sufficient amplitude for adapting the secondary path response.

The foregoing and other objectives, features, and advantages of the invention will be apparent from the following, more particular, description of the preferred embodiment of the invention, as illustrated in the accompanying drawings.

DESCRIPTION OF ILLUSTRATIVE EMBODIMENT

The present disclosure reveals noise canceling techniques and circuits that can be implemented in a personal audio device, such as wireless headphones or a wireless telephone. The personal audio device includes an adaptive noise canceling (ANC) circuit that measures the ambient acoustic environment and generates a signal that is injected into the speaker (or other transducer) output to cancel ambient acoustic events. A reference microphone is provided to measure the ambient acoustic environment, and an error microphone is included to measure the ambient audio and transducer output at the transducer, thus giving an indication of the effectiveness of the noise cancelation. A secondary path estimating adaptive filter is used to remove the playback audio from the error microphone signal, in order to generate an error signal. However, depending on the presence (and level) of the audio signal reproduced by the personal audio device, e.g., downlink audio during a telephone conversation or playback audio from a media file/connection, the secondary path adaptive filter may not be able to continue to adapt to estimate the secondary path. The circuits and methods disclosed herein use injected noise to provide enough energy for the secondary path estimating adaptive filter to continue to adapt, while remaining at a level that is less noticeable or unnoticeable to the listener.

The spectrum of the injected noise is altered by adapting a noise shaping filter that shapes the frequency spectrum of the noise in conformity with the frequency content of the error signal that represents the output of the transducer as heard by the listener with the playback audio (and thus also the injected noise) removed. The injected noise is also controlled in conformity with at least one parameter of the secondary path response, e.g., the gain and/or higher-order coefficients of the secondary path response. The result is that the amplitude of the injected noise will track the residual ambient noise as heard by the listener in different frequency bands, so that the secondary path estimating adaptive filter can be effectively trained, while maintaining the injected noise at an imperceptible level.

Figure 1A:
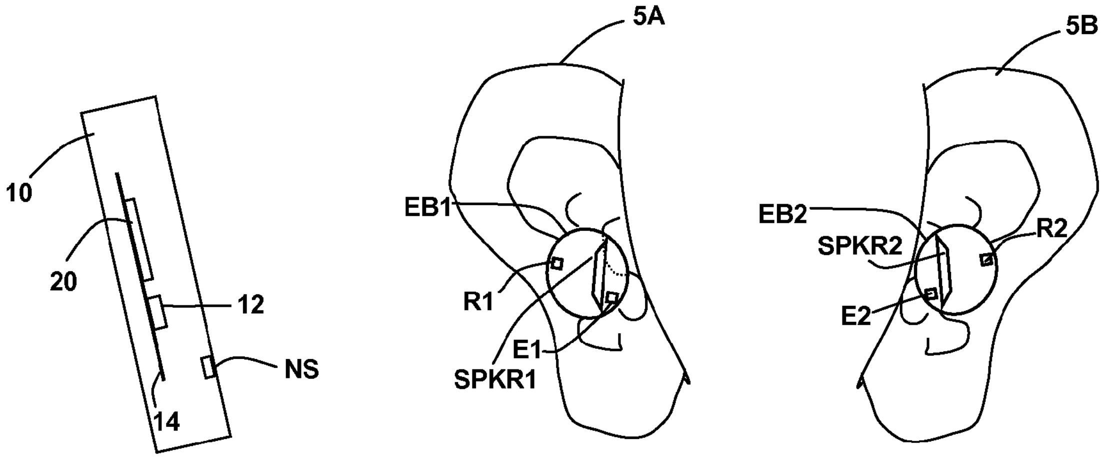
FIG. 1A is an illustration of a wireless telephone 10 coupled to a pair of earbuds EB1 and EB2, which is an example of a personal audio system in which the techniques disclosed herein can be implemented.

FIG. 1A shows a wireless telephone 10 and a pair of earbuds EB1 and EB2, each attached to a corresponding ear 5A, 5B of a listener. Illustrated wireless telephone 10 is an example of a device in which the techniques herein may be employed, but it is understood that not all of the elements or configurations illustrated in wireless telephone 10, or in the circuits depicted in subsequent illustrations, are required. Wireless telephone 10 is connected to earbuds EB1, EB2 by a wired or wireless connection, e.g., a BLUETOOTH™ connection (BLUETOOTH is a trademark of Bluetooth SIG, Inc.). Earbuds EB1, EB2 each have a corresponding transducer, such as speaker SPKR1, SPKR2, which reproduce source audio including distant speech received from wireless telephone 10, ringtones, stored audio program material, and injection of near-end speech (i.e., the speech of the user of wireless telephone 10). The source audio also includes any other audio that wireless telephone 10 is required to reproduce, such as source audio from web-pages or other network communications received by wireless telephone 10 and audio indications such as battery low and other system event notifications. Reference microphones R1, R2 are provided on a surface of the housing of respective earbuds EB1, EB2 for measuring the ambient acoustic environment. Another pair of microphones, error microphones E1, E2, are provided in order to further improve the ANC operation by providing a measure of the ambient audio combined with the audio reproduced by respective speakers SPKR1, SPKR2 close to corresponding ears 5A, 5B, when earbuds EB1, EB2 are inserted in the outer portion of ears 5A, 5B.

Wireless telephone 10 includes adaptive noise canceling (ANC) circuits and features that inject an anti-noise signal into speakers SPKR1, SPKR2 to improve intelligibility of the distant speech and other audio reproduced by speakers SPKR1, SPKR2. An exemplary circuit 14 within wireless telephone 10 includes an audio integrated circuit 20 that receives the signals from reference microphones R1, R2, a near speech microphone NS, and error microphones E1, E2 and interfaces with other integrated circuits such as a radio frequency (RF) integrated circuit 12 containing the wireless telephone transceiver. In other implementations, the circuits and techniques disclosed herein may be incorporated in a single integrated circuit that contains control circuits and other functionality for implementing the entirety of the personal audio device, such as an MP3 player-on-a-chip integrated circuit. Alternatively, the ANC circuits may be included within a housing of earbuds EB1, EB2 or in a module located along wired connections between wireless telephone 10 and earbuds EB1, EB2. In other embodiments, wireless telephone 10 includes a reference microphone, error microphone and speaker and the noise-canceling is performed by an integrated circuit within wireless telephone 10. For the purposes of illustration, the ANC circuits will be described as provided within wireless telephone 10, but the above variations are understandable by a person of ordinary skill in the art and the consequent signals that are required between earbuds EB1, EB2, wireless telephone 10, and a third module, if required, can be easily determined for those variations. A near speech microphone NS is provided at a housing of wireless telephone 10 to capture near-end speech, which is transmitted from wireless telephone 10 to the other conversation participant(s). Alternatively, near speech microphone NS may be provided on the outer surface of a housing of one of earbuds EB1, EB2, on a boom affixed to one of earbuds EB1, EB2, or on a pendant located between wireless telephone 10 and either or both of earbuds EB1, EB2.

Figure 1B:
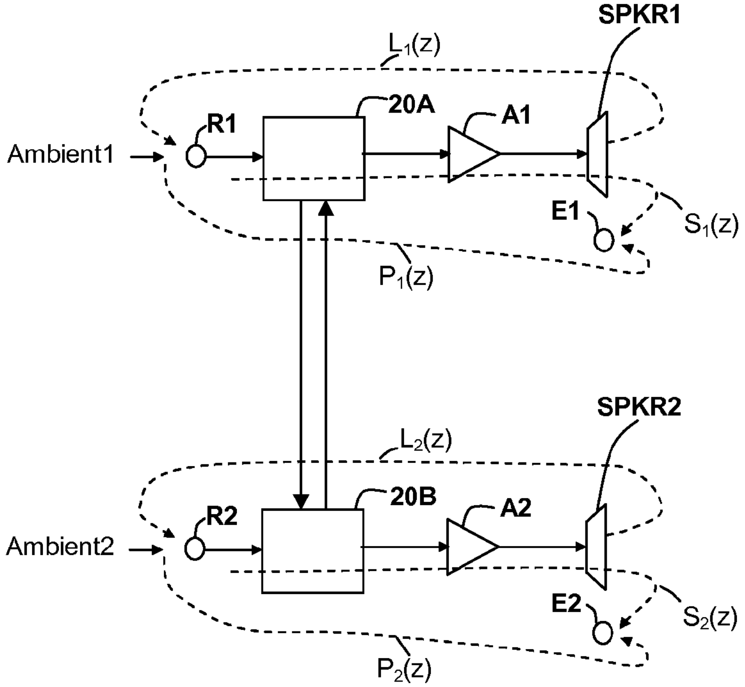
FIG. 1B is an illustration of electrical and acoustical signal paths in FIG. 1A.

FIG. 1B shows a simplified schematic diagram of audio integrated circuits 20A, 20B that include ANC processing, as coupled to respective reference microphones R1, R2, which provides a measurement of ambient audio sounds Ambient1, Ambient 2 that is filtered by the ANC processing circuits within audio integrated circuits 20A, 20B, located within corresponding earbuds EB1, EB2. Audio integrated circuits 20A, 20B may be alternatively combined in a single integrated circuit, such as integrated circuit 20 within wireless telephone 10. Audio integrated circuits 20A, 20B generate outputs for their corresponding channels that are amplified by an associated one of amplifiers A1, A2 and which are provided to the corresponding one of speakers SPKR1, SPKR2. Audio integrated circuits 20A, 20B receive the signals (wired or wireless depending on the particular configuration) from reference microphones R1, R2, near speech microphone NS and error microphones E1, E2. Audio integrated circuits 20A, 20B also interface with other integrated circuits such as an RF integrated circuit 12 containing the wireless telephone transceiver shown in FIG. 1A. In other configurations, the circuits and techniques disclosed herein may be incorporated in a single integrated circuit that contains control circuits and other functionality for implementing the entirety of the personal audio device, such as an MP3 player-on-a-chip integrated circuit. Alternatively, multiple integrated circuits may be used, for example, when a wireless connection is provided from each of earbuds EB1, EB2 to wireless telephone 10 and/or when some or all of the ANC processing is performed within earbuds EB1, EB2 or a module disposed along a cable connecting wireless telephone 10 to earbuds EB1, EB2.

In general, the ANC techniques illustrated herein measure ambient acoustic events (as opposed to the output of speakers SPKR1, SPKR2 and/or the near-end speech) impinging on reference microphones R1, R2 and also measure the same ambient acoustic events impinging on error microphones E1, E2. The ANC processing circuits of integrated circuits 20A, 20B individually adapt an anti-noise signal generated from the output of the corresponding reference microphone R1, R2 to have a characteristic that minimizes the amplitude of the ambient acoustic events at the corresponding error microphone E1, E2. Since acoustic path $P_1(z)$ extends from reference microphone R1 to error microphone E1, the ANC circuit in audio integrated circuit 20A is essentially estimating acoustic path $P_1(z)$ combined with removing effects of an electro-acoustic path $S_1(z)$ that represents the response of the audio output circuits of audio integrated circuit 20A and the acoustic/electric transfer function of speaker SPKR1. The estimated response includes the coupling between speaker SPKR1 and error microphone E1 in the particular acoustic environment which is affected by the proximity and structure of ear 5A and other physical objects and human head structures that may be in proximity to earbud EB1. Similarly, audio integrated circuit 20B estimates acoustic path $P_2(z)$ combined with removing effects of an electro-acoustic path $S_2(z)$ that represents the response of the audio output circuits of audio integrated circuit 20B and the acoustic/electric transfer function of speaker SPKR2.

Figure 2:
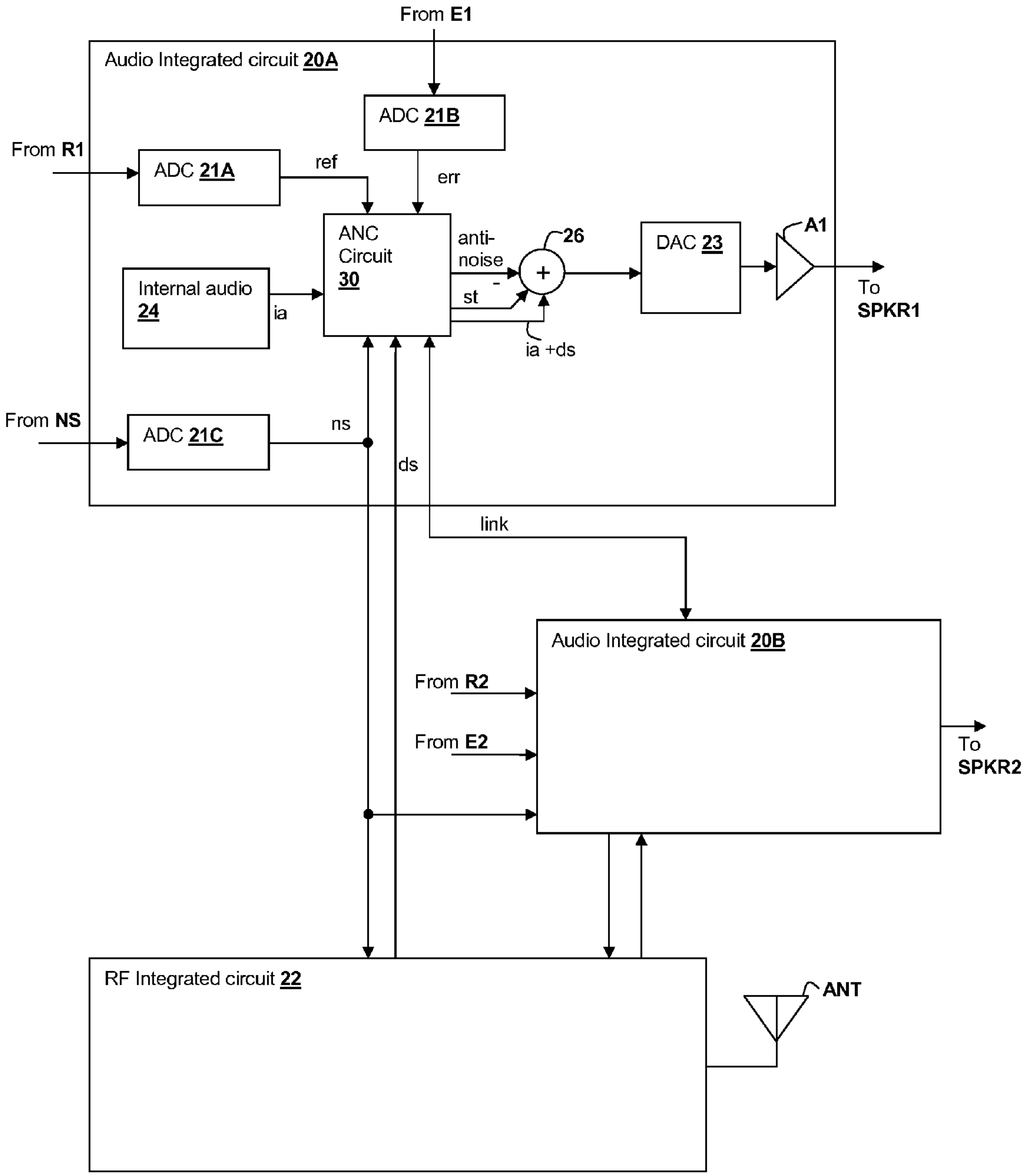
FIG. 2 is a block diagram of circuits within wireless telephone 10.

Referring now to FIG. 2, circuits within earbuds EB1, EB2 and wireless telephone 10 are shown in a block diagram. The circuit shown in FIG. 2 further applies to the other configurations mentioned above, except that signaling between CODEC integrated circuit 20 and other units within wireless telephone 10 are provided by cables or wireless connections when audio integrated circuits 20A, 20B are located outside of wireless telephone 10, e.g., within corresponding earbuds EB1, EB2. In such a configuration, signaling between a single integrated circuit 20 that implements integrated circuits 20A-20B and error microphones E1, E2, reference microphones R1, R2 and speakers SPKR1, SPKR2 are provided by wired or wireless connections when audio integrated circuit 20 is located within wireless telephone 10. In the illustrated example, audio integrated circuits 20A, 20B are shown as separate and substantially identical circuits, so only audio integrated circuit 20A will be described in detail below.

Audio integrated circuit 20A includes an analog-to-digital converter (ADC) 21A for receiving the reference microphone signal from reference microphone R1 and generating a digital representation ref of the reference microphone signal. Audio integrated circuit 20A also includes an ADC 21B for receiving the error microphone signal from error microphone E1 and generating a digital representation err of the error microphone signal, and an ADC 21C for receiving the near speech microphone signal from near speech microphone NS and generating a digital representation of near speech microphone signal ns. (Audio integrated circuit 20B receives the digital representation of near speech microphone signal ns from audio integrated circuit 20A via the wireless or wired connections as described above.) Audio integrated circuit 20A generates an output for driving speaker SPKR1 from an amplifier A1, which amplifies the output of a digital-to-analog converter (DAC) 23 that receives the output of a combiner 26. Combiner 26 combines audio signals ia from internal audio sources 24, and the anti-noise signal anti-noise generated by an ANC circuit 30, which by convention has the same polarity as the noise in reference microphone signal ref and is therefore subtracted by combiner 26. Combiner 26 also combines an attenuated portion of near speech signal ns, i.e., sidetone information st, so that the user of wireless telephone 10 hears their own voice in proper relation to downlink speech ds, which is received from a radio frequency (RF) integrated circuit 22. Near speech signal ns is also provided to RF integrated circuit 22 and is transmitted as uplink speech to the service provider via an antenna ANT.

Figure 3:
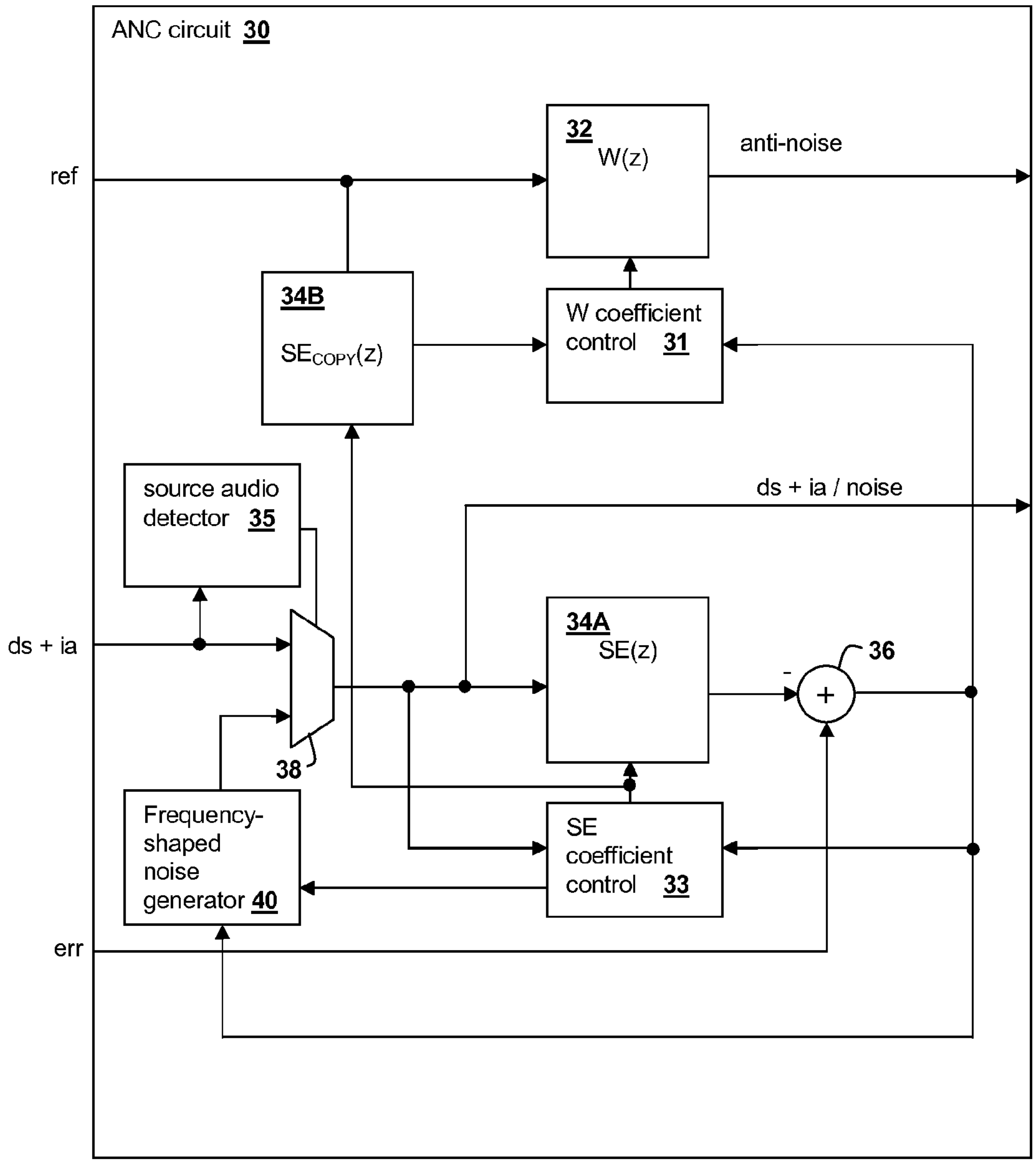
FIG. 3 is a block diagram depicting signal processing circuits and functional blocks within ANC circuit 30 of CODEC integrated circuit 20 of FIG. 2.

Referring now to FIG. 3, details of an exemplary ANC circuit 30 within audio integrated circuits 20A and 20B of FIG. 2, are shown. An adaptive filter 32 receives reference microphone signal ref and under ideal circumstances, adapts its transfer function W(z) to be P(z)/S(z) to generate the anti-noise signal anti-noise, which is provided to an output combiner that combines the anti-noise signal with the audio to be reproduced by the transducer, as exemplified by combiner 26 of FIG. 2. The coefficients of adaptive filter 32 are controlled by a W coefficient control block 31 that uses a correlation of two signals to determine the response of adaptive filter 32, which generally minimizes the error, in a least-mean squares sense, between those components of reference microphone signal ref present in error microphone signal err. The signals processed by W coefficient control block 31 are the reference microphone signal ref as shaped by a copy of an estimate of the response of path S(z) provided by filter 34B and another signal that includes error microphone signal err. By transforming reference microphone signal ref with a copy of the estimate of the response of path S(z), response $SE_{COPY}(z)$, and minimizing error microphone signal err after removing components of error microphone signal err due to playback of source audio, adaptive filter 32 adapts to the desired response of P(z)/S(z). In addition to error microphone signal err, the other signal processed along with the output of a filter 34B by W coefficient control block 31 includes an inverted amount of the source audio including downlink audio signal ds and internal audio ia that has been processed by filter response SE(z), of which response $SE_{COPY}(z)$ is a copy. By injecting an inverted amount of source audio, adaptive filter 32 is prevented from adapting to the relatively large amount of source audio present in error microphone signal err and by transforming the inverted copy of downlink audio signal ds and internal audio ia with the estimate of the response of path S(z), the source audio that is removed from error microphone signal err before processing should match the expected version of downlink audio signal ds, and internal audio ia reproduced at error microphone signal err, since the electrical and acoustical path of S(z) is the path taken by downlink audio signal ds and internal audio ia to arrive at error microphone E. Filter 34B is not an adaptive filter, per se, but has an adjustable response that is tuned to match the response of an adaptive filter 34A, so that the response of filter 34B tracks the adapting of adaptive filter 34A.

To implement the above, adaptive filter 34A has coefficients controlled by a SE coefficient control block 33, which processes the source audio (ds+ia) and error microphone signal err after removal, by a combiner 36, of the above-described filtered downlink audio signal ds and internal audio ia, that has been filtered by adaptive filter 34A to represent the expected source audio delivered to error microphone E. Adaptive filter 34A is thereby adapted to generate a signal from downlink audio signal ds and internal audio ia, that when subtracted from error microphone signal err, contains the content of error microphone signal err that is not due to source audio (ds+ia). However, if downlink audio signal ds and internal audio ia are both absent, or have very low amplitude, SE coefficient control block 33 will not have sufficient input to estimate acoustic path S(z). Therefore, in ANC circuit 30, a source audio detector 35 detects whether sufficient source audio (ds+ia) is present, and updates the secondary path estimate if sufficient source audio (ds+ia) is present. Source audio detector 35 may be replaced by a speech presence signal if such is available from a digital source of the downlink audio signal ds, or a playback active signal provided from media playback control circuits. A selector 38 selects the output of a frequency-shaped noise generator 40 if source audio (ds+ia) is absent or low in amplitude, which provides output ds+ia/noise to combiner 26 of FIG. 2, and an input to secondary path adaptive filter 34A and SE coefficient control block 33, allowing ANC circuit 30 to maintain estimating acoustic path S(z). Alternatively, selector 38 can be replaced with a combiner that adds the noise signal to source audio (ds+ia).

When source audio (ds+ia) is absent, speaker SPKR of FIG. 1 will actually reproduce noise injected from frequency-shaped noise generator 40, and thus it would be undesirable for the user of the device to hear the injected noise. Therefore, frequency-shaped noise generator 40 shapes the frequency spectrum of the generated noise signal by observing the error signal generated from the output of secondary path adaptive filter 34A. The error signal provides a good estimate of the spectrum of the ambient noise, which affects the amount of injected noise that the user actually hears. The injected noise heard by the listener is transformed by path S(z) Therefore, frequency-shaped noise generator 40 uses at least a portion of the coefficients of secondary-path filter response SE(z) as generated by SE coefficient control block 33 to determine an adaptive noise-shaping filter response that is applied to the injected noise generated by frequency-shaped noise generator 40.

Figure 4:
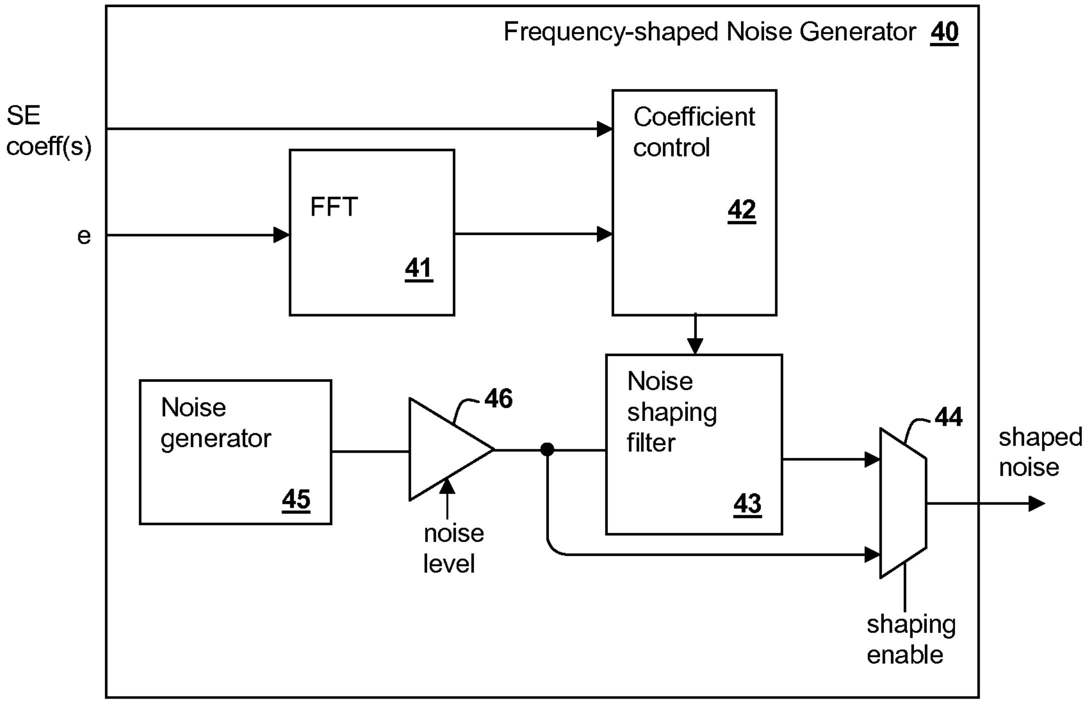
FIG. 4 is a block diagram depicting details of frequency-shaping noise generator 40 of FIG. 3.

Referring now to FIG. 4, details of frequency-shaped noise generator 40 are shown. A fast-fourier transform (FFT) block 41 determines frequency content of error signal e and provides information to a coefficient control block 42. Coefficient control block 42 also receives at least some of the coefficient information generated by SE coefficient control block 33, which in some implementations is only the gain of secondary path filter response SE(z) and in other implementations is the entire secondary path filter response SE(z). The output of coefficient control 42 adaptively controls a noise-shaping filter 43 that filters the output of a noise generator 45 that generally has a uniform spectrum, e.g., white noise. In general, noise-shaping filter 43 is adapted to have the same power spectral density (PSD) as error signal e. A gain control block 46 controls an amplitude of the noise signal as provided to noise shaping filter 43, according to a control value noise level. A selector 44 selects between the output of noise shaping filter 43 and the output of gain control block 46 according to a control signal shaping enable that is set or reset according to an operating mode of the personal audio device. Further details of operation of frequency-shaped noise generator 40 are described below.

Figure 5:
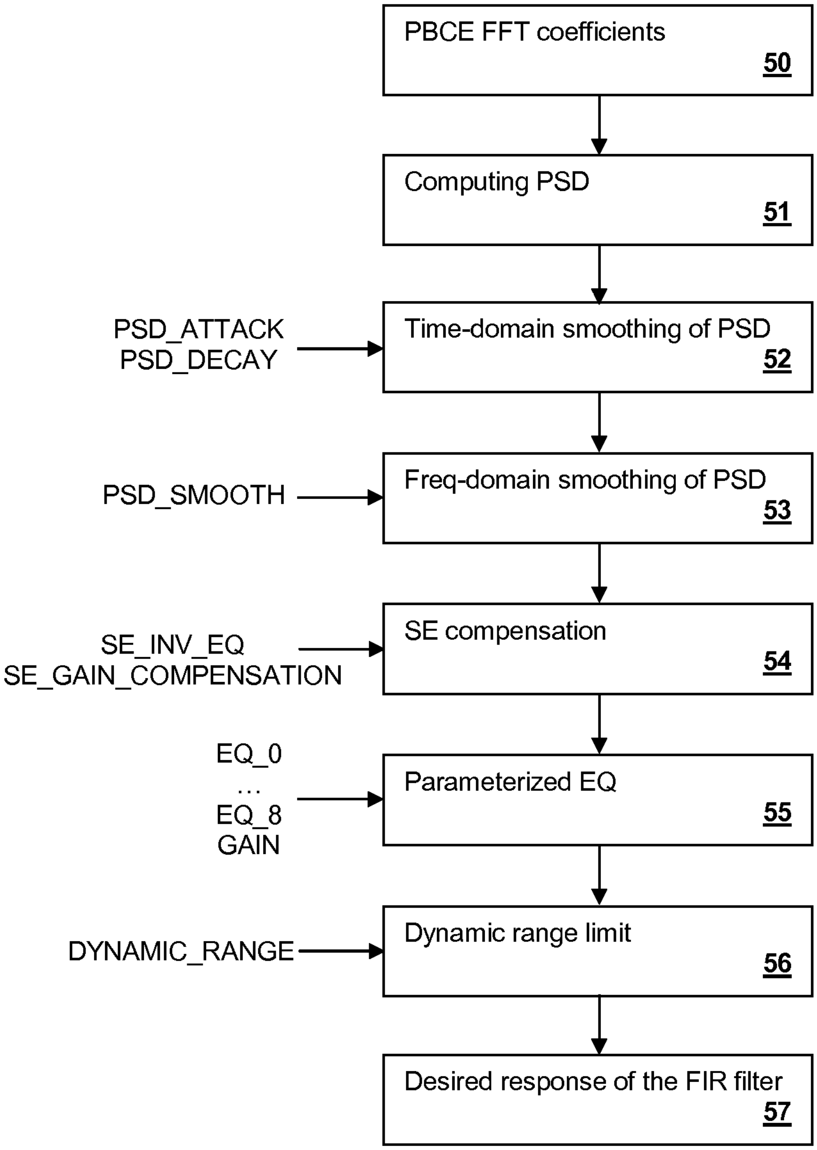
FIG. 5-FIG. 7 are process diagrams showing computations performed in the operation of frequency-shaping noise generator 40 of FIG. 3.

Referring now to FIG. 5, a process for determining the desired frequency response of noise shaping filter 43 is illustrated, as may be performed by coefficient control block 42 of FIG. 4. The power spectral density (PSD) of error signal e is determined by FFT block 41 in steps 50-51. The resulting PSD coefficients are smoothed in the time domain (step 52), by a smoothing algorithm with rise-time determined by control value PSD_ATTACK and a fall-time determined by control value PSD_DECAY. An example smoothing algorithm that can be used for performing the time-domain smoothing of step 52 is given by:

$$P(k,n)=a_t P(k,n-1)+(1-a_t)|e(k)|^2,$$

where P(k, n) is the computed PSD of error signal e, $a_t$ is a time-domain smoothing coefficient and k is a frequency bin number corresponding to the FFT coefficient. The time-domain smoothed PSD is smoothed in the frequency domain (step 53) by a frequency-smoothing algorithm controlled by control value PSD_SMOOTH. An example frequency smoothing algorithm may smooth the PSD spectrum from a lowest-frequency bin and proceeding to a highest-frequency bin, as in the following equation, $$P'(k+1)=a_f P'(k)+(1-a_f)P(k+1)$$

Where P is the PSD of error signal after time-domain smoothing, P' is the PSD of error signal e after frequency-domain smoothing, k denotes the frequency bin and $a_f$ is a frequency-domain smoothing coefficient. After smoothing in the frequency domain by increasing frequency bin, the PSD of error signal e is smoothed starting from the highest-frequency bin and ending at the lowest-frequency bin as exemplified by the following equation:

$$P''(k-1)=a_f P''(k)+(1-a_f)P'(k-1),$$

where P"(k) is the final frequency-smoothed PSD result for bin k. The smoothing performed in steps 52-53 ensures that abrupt changes and narrowband frequency spikes due to narrowband signals present in error signal e are removed from the resulting processed PSD.

Once frequency smoothing is complete, the time- and frequency-smoothed PSD is altered according to at least one coefficient of an estimated secondary-path response as determined by coefficients of secondary-path adaptive filter 34A of FIG. 3, which may be a gain adjustment as determined by a control value SE_GAIN_COMPENSATION, or a frequency dependent response modeling the inverse of the estimated secondary response SE_INV_EQ (step 54). In one example, the smoothed PSD of error signal e, P"(k), is transformed by the inverse $C_{SE\_inv}$ of the response SE(z) in the frequency band corresponding to bin k:

$$\hat{P}(k)=P''(k)\cdot C_{SE\_inv}(k)$$

The gain of response SE(z) is also compensated for by multiplying the SE-compensated PSD $\hat{P}(k)$ by a gain factor $G_{SE\_gain\_inv}$:

$$\hat{P}(k)=\hat{P}(k)\cdot G_{SE\_gain\_inv}$$

Next a predetermined parametric equalization is applied according to control values EQ_0-EQ_8 (step 55), which can simplify the design of the finite impulse response (FIR) filter used to implement noise-shaping filter 43, and compression is applied to the equalized noise in order to limit the dynamic range of the resulting PSD according to a control value DYNAMIC_RANGE (step 56). The resulting processed PSD of error signal e is used as the target frequency response for noise-shaping filter 43, which in the depicted embodiment is a FIR filter controlled by coefficient control 42 according to the output of FFT block 41 (step 57). The amplitude of the frequency response of the FIR filter used to implement noise-shaping filter 43 is given by:

$$A(k)=\sqrt{\hat{P}(k)}$$

Figure 6:
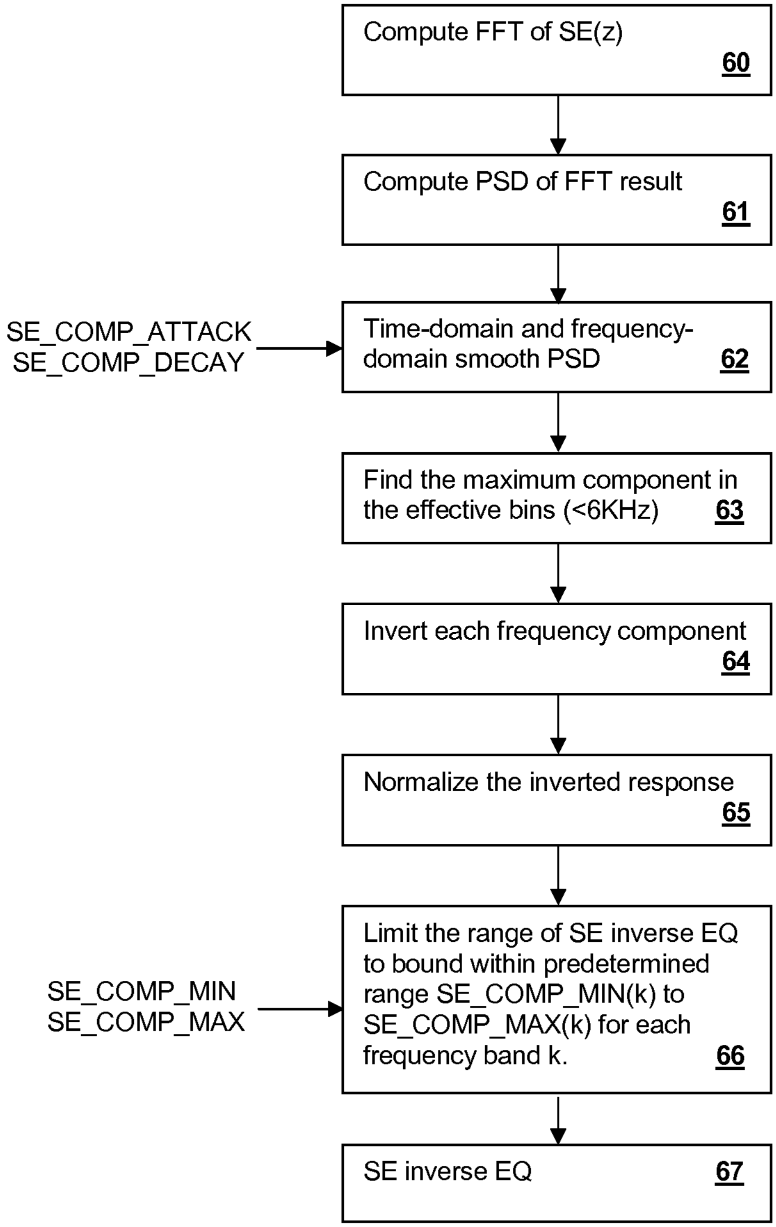

Referring now to FIG. 6, a process for determining the normalized inverse of response SE(z) is illustrated. First, an FFT of response SE(z) is computed (step 60), and the PSD of response SE(z) is computed (step 61) and smoothed in the time and frequency domains according to a rise-time control value SE_COMP_ATTACK and a fall-time control value SE_COMP_DECAY (step 62). Then the maximum component of the FFE is found for each of the bins below a cutoff frequency, e.g., 6 kHz (step 63) and each frequency component is inverted (step 64). Half of the maximum value for each bin is added to the resulting response (step 65) and a limitation is applied to bound the inverse of the computed SE(z) response within ranges [SE_COMP_MIN(k):SE_COMP_MAX(k)] for each frequency band k (step 66), providing the resulting equalization values corresponding to the inverse of SE(z) (step 67).

Figure 7:
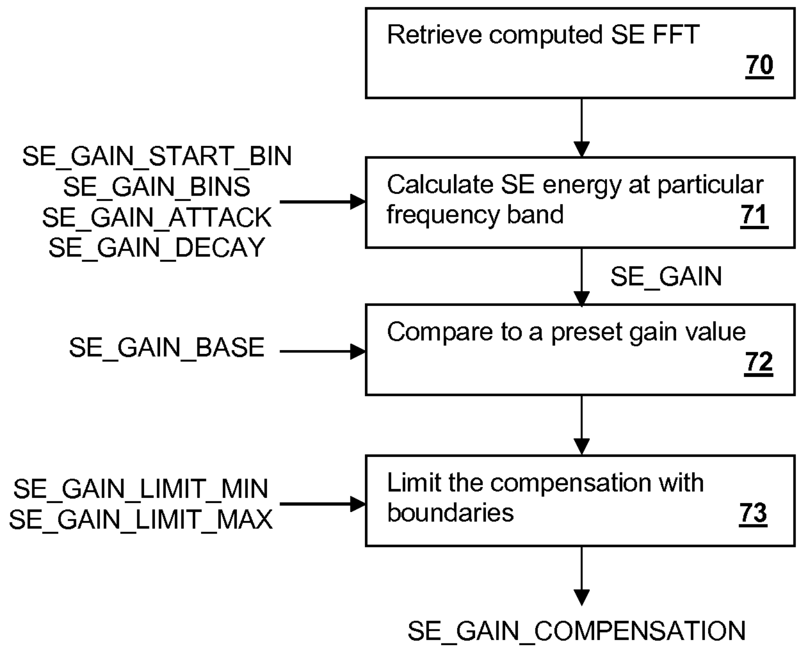

Referring now to FIG. 7, a process for normalizing the gain of the inverse of SE(z) is shown. First, the computed FFT of response SE(z) from step 60 of FIG. 6 is retrieved (step 70), and the energy of the FFT is computed for particular frequency bins SE_GAIN_BINS (step 61) and smoothed in the time-domain according to rise-time value SE_GAIN_ATTACK and fall-time value SE_GAIN_DECAY (step 71). The resulting gain value is compared to a preset gain value (step 72) and limited according to a bounded range from SE_GAIN_LIMIT_MIN to SE_GAIN_LIMIT_MAX (step 73).

Figure 8:
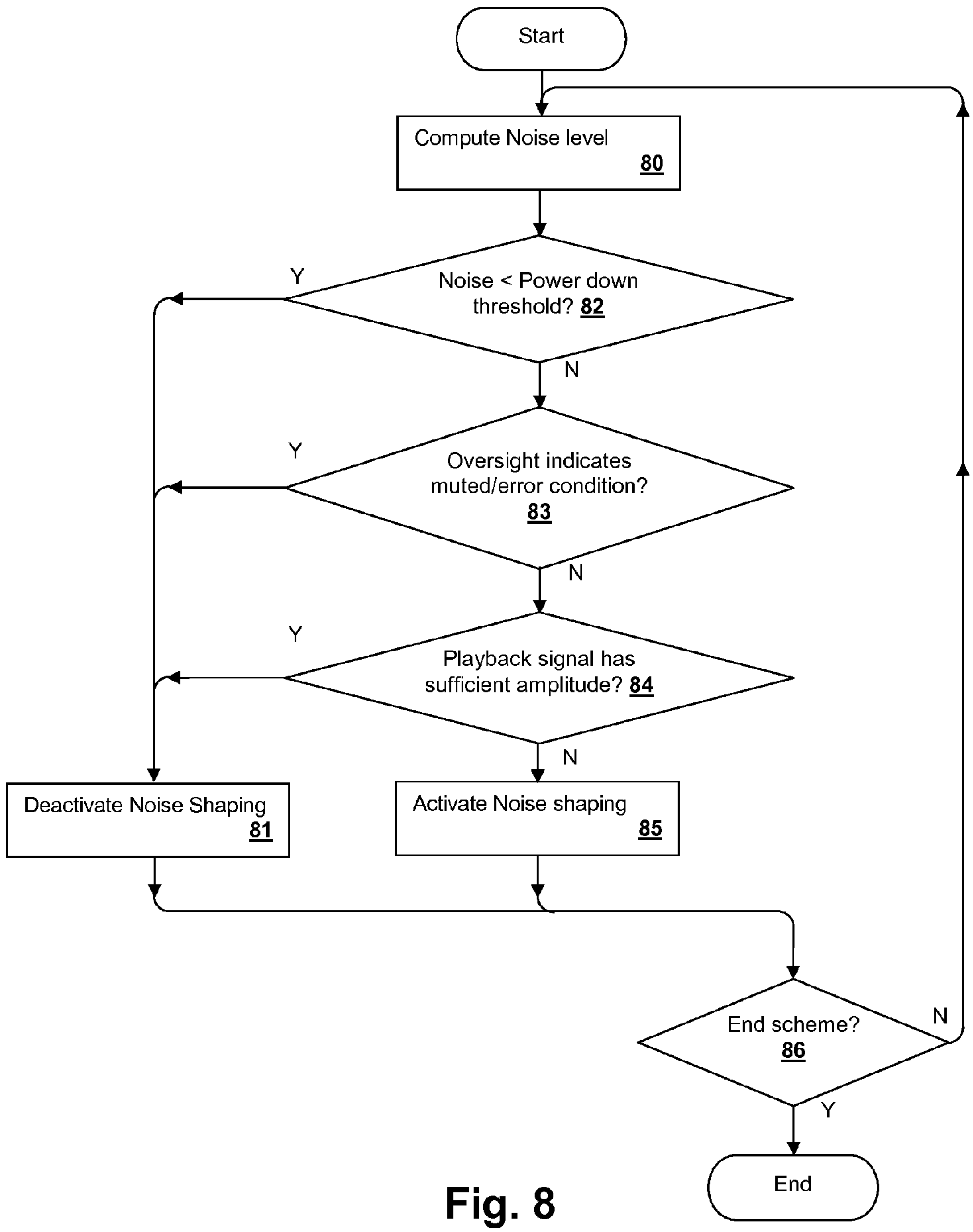
FIG. 8 is a flowchart showing other details of the operation of frequency-shaping noise generator 40 of FIG. 3.

Referring now to FIG. 8, a process for determining when to activate the noise shaping by asserting control signal shaping enable of FIG. 4 is shown in a flow chart. First, the noise level is computed (step 80) and compared to a power-down threshold (decision 82). If the noise level is below the power-down threshold (decision 82), then the noise shaping is deactivated (step 81). Also if ANC oversight system indicates muted or other error conditions (decision 83), noise shaping is deactivated (step 81). Oversight of ANC systems is described in more detail in published U.S. Patent Application US20120140943A1 entitled "OVERSIGHT CONTROL OF AN ADAPTIVE NOISE CANCELER IN A PERSONAL AUDIO DEVICE", the disclosure of which is incorporated herein by reference. Finally, if the playback audio signal has sufficient amplitude (decision 84), then noise shaping is deactivated (step 81). If none of the above conditions apply for deactivating noise shaping, then noise shaping is activated (step 85). Until the scheme is ended or the system is shut down (decision 86), steps 80-85 are repeated.

Figure 9:
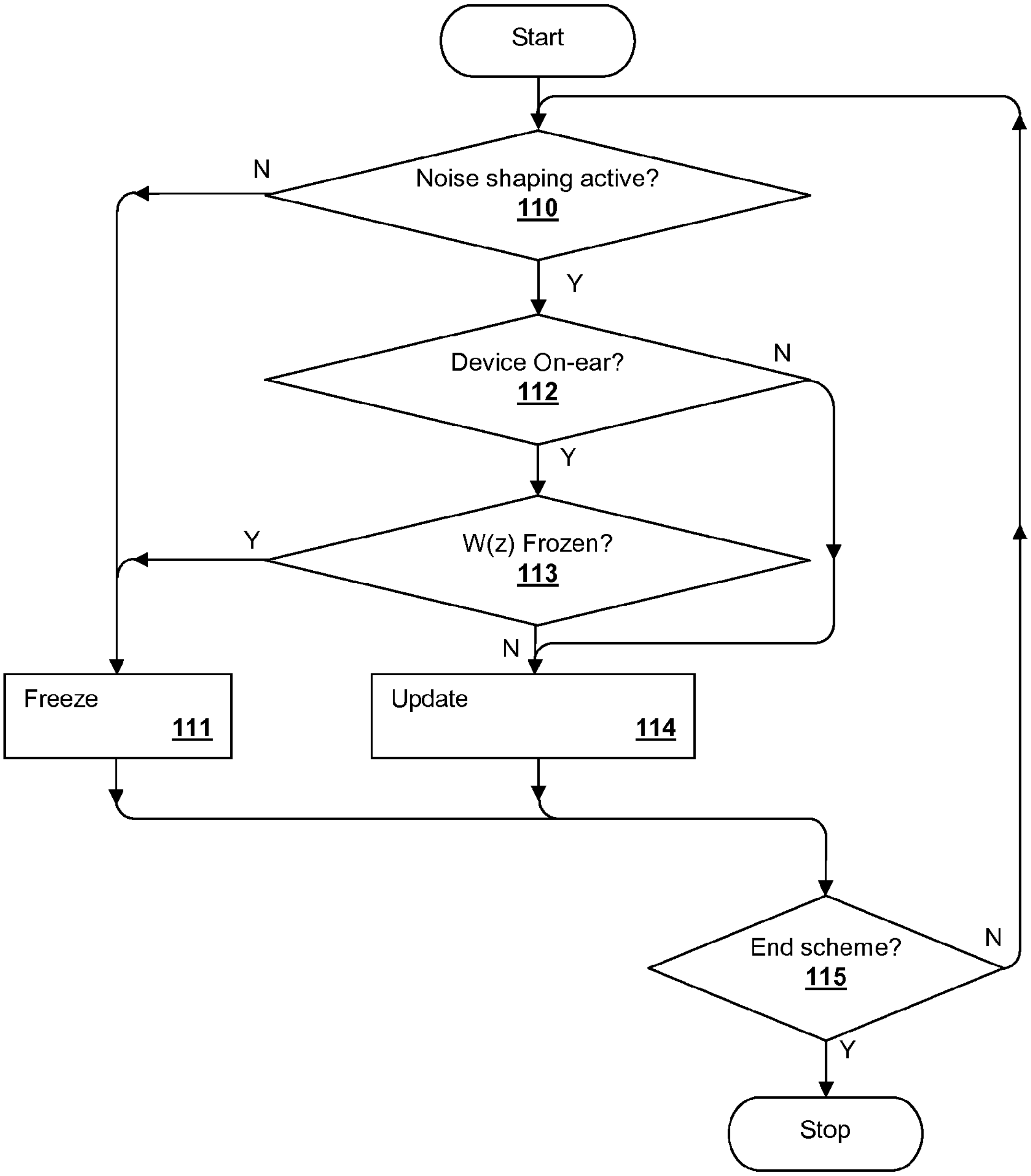
FIG. 9 is a flowchart showing further details of operation of frequency-shaping noise generator 40 of FIG. 3.

Referring now to FIG. 9, a process for throttling the process of the design of the FIR filter that implements noise-shaping filter 43 is shown in a flowchart. If noise-shaping is inactive (decision 110), the design process shown in FIG. 5 is halted (step 111). If noise-shaping is active (decision 110) and the device is on-ear (decision 112), and if response W(z) is frozen (i.e., W coefficient control block 31 of FIG. 3 is actively updating response W(z) of adaptive filter 32 of FIG. 3) (decision 113), then, the design process shown in FIG. 5 is also halted (step 111). Otherwise, if noise-shaping is active and the device is off-ear (decision 112), or the device is on-ear (decision 112) and response W(z) is not frozen, then the filter design is updated according to the process of FIG. 5 (step 114). Until the scheme is ended, or the system is shut down (decision 115), steps 110-114 are repeated.

Figure 10:
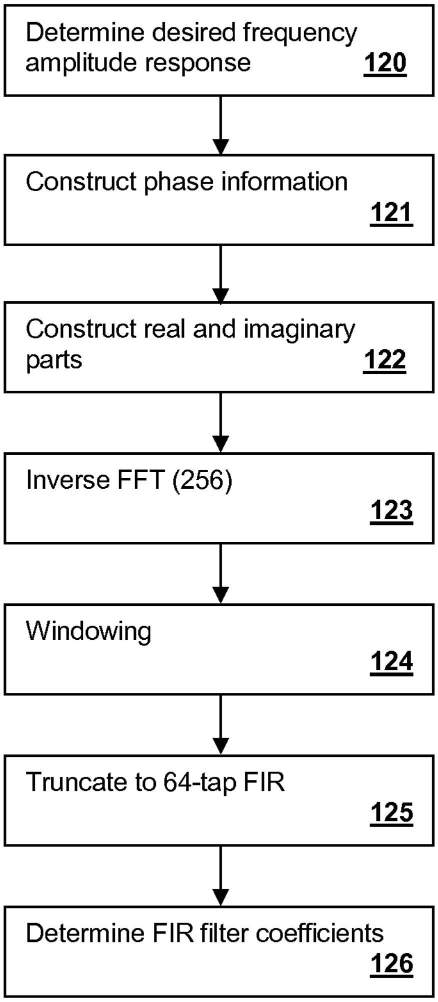
FIG. 10 is a process diagram showing other computations performed in the operation of frequency-shaping noise generator 40 of FIG. 3.

Referring now to FIG. 10, a process for determining the FIR filter coefficients for implementing the response determined by the process of FIG. 5 is shown. The desired frequency-dependent amplitude response is determined (step 120), e.g., by performing the process of FIG. 5. The phase information is constructed (step 121) and real and imaginary parts of the response are determined (step 122). An inverse FFT is computed (step 123), and a windowing function is applied (step 124). The filter design is then truncated to a 64-tap FIR filter (step 125) and the FIR filter coefficients are applied from the truncated filter design (step 126)

Figure 11:
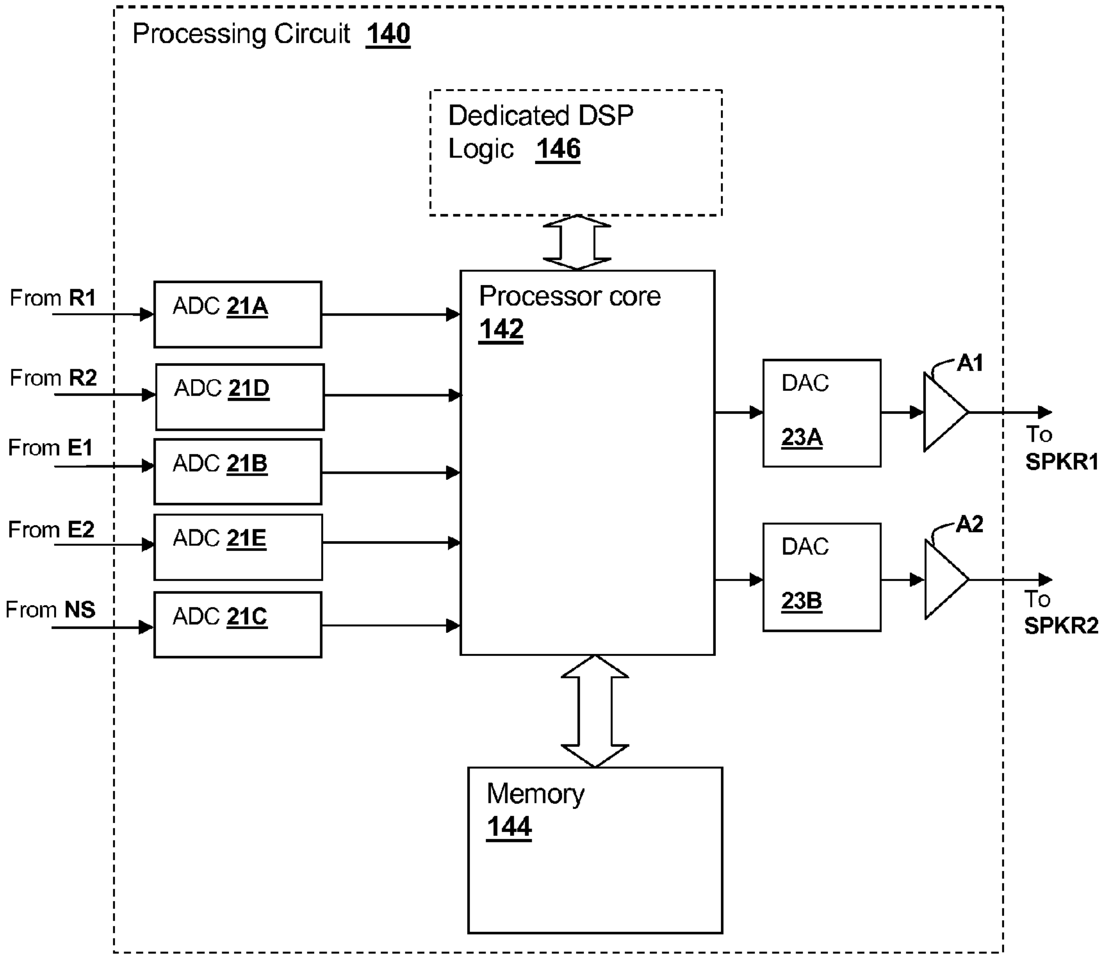
FIG. 11 is a block diagram depicting signal processing circuits and functional blocks within an integrated circuit implementing an ANC system as disclosed herein.

Referring now to FIG. 11, a block diagram of an ANC system is shown for implementing ANC techniques as depicted in FIG. 3 and having a processing circuit 140 as may be implemented within audio integrated circuits 20A, 20B of FIG. 2, which is illustrated as combined within one circuit, but could be implemented as two or more processing circuits that inter-communicate. Processing circuit 140 includes a processor core 142 coupled to a memory 144 in which are stored program instructions comprising a computer program product that may implement some or all of the above-described ANC techniques, as well as other signal processing. Optionally, a dedicated digital signal processing (DSP) logic 146 may be provided to implement a portion of, or alternatively all of, the ANC signal processing provided by processing circuit 140. Processing circuit 140 also includes ADCs 21A-21E, for receiving inputs from reference microphone R1, error microphone E1 near speech microphone NS, reference microphone R2, and error microphone E2, respectively. In alternative embodiments in which one or more of reference microphone R1, error microphone E1 near speech microphone NS, reference microphone R2, and error microphone E2 have digital outputs or are communicated as digital signals from remote ADCs, the corresponding ones of ADCs 21A-21E are omitted and the digital microphone signal(s) are interfaced directly to processing circuit 140. A DAC 23A and amplifier A1 are also provided by processing circuit 140 for providing the speaker output signal to speaker SPKR1, including anti-noise as described above. Similarly, a DAC 23B and amplifier A2 provide another speaker output signal to speaker SPKR2. The speaker output signals may be digital output signals for provision to modules that reproduce the digital output signals acoustically.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. A personal audio device, comprising:

a personal audio device housing;

a transducer mounted on the housing for reproducing an audio signal including both source audio for playback to a listener and an anti-noise signal for countering the effects of ambient audio sounds in an acoustic output of the transducer;

a reference microphone mounted on the housing for providing a reference microphone signal indicative of the ambient audio sounds;

an error microphone mounted on the housing in proximity to the transducer for providing an error microphone signal indicative of the acoustic output of the transducer and the ambient audio sounds at the transducer;

a controllable noise source for providing a noise signal; and a processing circuit that filters the reference microphone signal with a first adaptive filter to generate the anti-noise signal to reduce the presence of the ambient audio sounds heard by the listener in conformity with an error signal and the reference microphone signal, wherein the processing circuit implements a noise shaping filter having a controllable frequency response that filters the noise signal to produce a frequency-shaped noise signal, wherein the processing circuit implements a secondary path adaptive filter having a secondary path response that shapes the source audio and a combiner that removes the source audio from the error microphone signal to provide the error signal, and wherein the processing circuit injects the frequency-shaped noise signal into the secondary path adaptive filter and the audio signal reproduced by the transducer in place of or in combination with the source audio to cause the secondary path adaptive filter to continue to adapt when the source audio is absent or has reduced amplitude, and wherein the processing circuit controls the frequency response of the noise shaping filter in conformity with at least one parameter of the secondary path response to reduce audibility of the noise signal in the audio signal reproduced by the transducer.

2. The personal audio device of claim 1, wherein the processing circuit analyzes the error signal to determine frequency content of the error signal and adaptively controls the controllable frequency response of the noise shaping filter in conformity with the frequency content of the error signal.

3. The personal audio device of claim 2, wherein the controllable response of the noise shaping filter includes a response that is an inverse of at least a portion of the secondary path response, wherein the at least one parameter comprises parameters determinative of the secondary path response.

4. The personal audio device of claim 2, wherein a gain of the controllable frequency response of the noise shaping filter is set in conformity with an inverse of a magnitude of the secondary path response over at least a portion of the secondary path response.

5. The personal audio device of claim 1, wherein a gain of the controllable frequency response of the noise shaping filter is set in conformity with an inverse of a magnitude of the secondary path response in a particular frequency band.

6. The personal audio device of claim 1, wherein the processing circuit further frequency-smooths the controllable frequency response of the noise shaping to prevent generation of narrow peaks in a frequency spectrum of the frequency-shaped noise signal.

7. The personal audio device of claim 1, wherein the processing circuit further smooths the controllable frequency response of the noise shaping in the time domain to prevent abrupt changes in the amplitude of the frequency-shaped noise signal.

8. The personal audio device of claim 1, wherein the processing circuit further reduces a rate of update of the controllable frequency response of the noise shaping filter in response to an indication of system instability or an ambient audio condition that may cause improper generation of that anti-noise signal.

9. A method of countering effects of ambient audio sounds by a personal audio device, the method comprising:

measuring the ambient audio sounds with a reference microphone to generate a reference microphone signal;

filtering the reference microphone signal with a first adaptive filter to generate an anti-noise signal to reduce the presence of the ambient audio sounds heard by the listener in conformity with an error signal and the reference microphone signal;

combining the anti-noise signal with source audio;

providing a result of the combining to a transducer;

measuring an acoustic output of the transducer and the ambient audio sounds with an error microphone;

shaping the source audio with a secondary path adaptive filter;

removing the source audio from the error microphone signal to provide the error signal;

generating a noise signal with a controllable noise source;

filtering the noise signal with a noise shaping filter having a controllable frequency response to produce a frequency-shaped noise signal;

injecting the frequency-shaped noise signal into the secondary path adaptive filter and the audio signal reproduced by the transducer in place of or in combination with the source audio to cause the secondary path adaptive filter to continue to adapt when the source audio is absent or has reduced amplitude; and controlling the frequency response of the noise shaping filter in conformity with at least one parameter of the secondary path response to reduce audibility of the noise signal in the audio signal reproduced by the transducer.

10. The method of claim 9, further comprising analyzing the error signal to determine frequency content of the error signal and wherein the controlling adaptively controls the controllable frequency response of the noise shaping filter in conformity with the frequency content of the error signal.

11. The method of claim 10, wherein the controllable response of the noise shaping filter includes a response that is an inverse of at least a portion of the secondary path response, wherein the at least one parameter comprises parameters determinative of the secondary path response.

12. The method of claim 10, wherein the controlling sets a gain of the controllable frequency response of the noise shaping filter in conformity with an inverse of a magnitude of the secondary path response over at least a portion of the secondary path response.

13. The method of claim 9, wherein the controlling sets a gain of the controllable frequency response of the noise shaping filter in conformity with an inverse of a magnitude of the secondary path response in a particular frequency band.

14. The method of claim 9, wherein the controlling further comprises smoothing the controllable frequency response of the noise shaping to prevent generation of narrow peaks in a frequency spectrum of the frequency-shaped noise signal.

15. The method of claim 9, wherein the controlling further comprises smoothing the controllable frequency response of the noise shaping in the time domain to prevent abrupt changes in the amplitude of the frequency-shaped noise signal.

16. The method of claim 9, further comprising reducing a rate of update of the controllable frequency response of the noise shaping filter in response to an indication of system instability or an ambient audio condition that may cause improper generation of that anti-noise signal.

17. An integrated circuit for implementing at least a portion of a personal audio device, comprising:

an output for providing an output signal to an output transducer including both source audio for playback to a listener and an anti-noise signal for countering the effects of ambient audio sounds in an acoustic output of the transducer;

a reference microphone input for receiving a reference microphone signal indicative of the ambient audio sounds;

an error microphone input for receiving an error microphone signal indicative of the acoustic output of the transducer and the ambient audio sounds at the transducer;

a controllable noise source for providing a noise signal; and a processing circuit that filters the reference microphone signal with a first adaptive filter to generate the anti-noise signal to reduce the presence of the ambient audio sounds heard by the listener in conformity with an error signal and the reference microphone signal, wherein the processing circuit implements a noise shaping filter having a controllable frequency response that filters the noise signal to produce a frequency-shaped noise signal, wherein the processing circuit implements a secondary path adaptive filter having a secondary path response that shapes the source audio and a combiner that removes the source audio from the error microphone signal to provide the error signal, and wherein the processing circuit injects the frequency-shaped noise signal into the secondary path adaptive filter and the audio signal reproduced by the transducer in place of or in combination with the source audio to cause the secondary path adaptive filter to continue to adapt when the source audio is absent or has reduced amplitude, and wherein the processing circuit controls the frequency response of the noise shaping filter in conformity with at least one parameter of the secondary path response to reduce audibility of the noise signal in the audio signal reproduced by the transducer.

18. The integrated circuit of claim 17, wherein the processing circuit analyzes the error signal to determine frequency content of the error signal and adaptively controls the controllable frequency response of the noise shaping filter in conformity with the frequency content of the error signal.

19. The integrated circuit of claim 18, wherein the controllable response of the noise shaping filter includes a response that is an inverse of at least a portion of the secondary path response, wherein the at least one parameter comprises parameters determinative of the secondary path response.

20. The integrated circuit of claim 18, wherein a gain of the controllable frequency response of the noise shaping filter is set in conformity with an inverse of a magnitude of the secondary path response over at least a portion of the secondary path response.

21. The integrated circuit of claim 17, wherein a gain of the controllable frequency response of the noise shaping filter is set in conformity with an inverse of a magnitude of the secondary path response in a particular frequency band.

22. The integrated circuit of claim 17, wherein the processing circuit further frequency-smooths the controllable frequency response of the noise shaping to prevent generation of narrow peaks in a frequency spectrum of the frequency-shaped noise signal.

23. The integrated circuit of claim 17, wherein the processing circuit further smooths the controllable frequency response of the noise shaping in the time domain to prevent abrupt changes in the amplitude of the frequency-shaped noise signal.

24. The integrated circuit of claim 17, wherein the processing circuit further reduces a rate of update of the controllable frequency response of the noise shaping filter in response to an indication of system instability or an ambient audio condition that may cause improper generation of that anti-noise signal.

* * * * *